US010888576B2

(12) United States Patent
Baier et al.

(10) Patent No.: US 10,888,576 B2
(45) Date of Patent: *Jan. 12, 2021

(54) COMPOSITION OF HMB AND ATP AND METHODS OF USE

(71) Applicant: Metabolic Technologies, Inc., Ames, IA (US)

(72) Inventors: Shawn Baier, Polk City, IA (US); Larry Kolb, Missoula, MT (US); John Rathmacher, Story City, IA (US)

(73) Assignee: Metabolic Technologies, Inc., Ames, IA (US)

( * ) Notice: Subject to any disclaimer, the term of this patent is extended or adjusted under 35 U.S.C. 154(b) by 23 days.

This patent is subject to a terminal disclaimer.

(21) Appl. No.: 16/154,387

(22) Filed: Oct. 8, 2018

(65) Prior Publication Data
US 2020/0108090 A1    Apr. 9, 2020

(51) Int. Cl.
    A61K 31/706    (2006.01)
    A61K 31/19     (2006.01)
    A61P 21/06     (2006.01)
    A61K 31/7076   (2006.01)

(52) U.S. Cl.
    CPC .......... *A61K 31/7076* (2013.01); *A61K 31/19* (2013.01); *A61P 21/06* (2018.01)

(58) Field of Classification Search
    None
    See application file for complete search history.

(56) References Cited

U.S. PATENT DOCUMENTS

| 10,092,590 B2 * | 10/2018 | Baier ................. A61K 31/7076 |
| 2005/0027005 A1 | 2/2005  | Boldt |
| 2005/0261238 A1 | 11/2005 | Lee et al. |
| 2006/0083793 A1 | 4/2006  | Gardiner et al. |
| 2007/0093553 A1 | 4/2007  | Baxter et al. |
| 2012/0053240 A1 | 3/2012  | Rathmacher et al. |

FOREIGN PATENT DOCUMENTS

| JP | 2001-314172 A    | 11/2001 |
| WO | WO 2006034586 A1 | 4/2006  |
| WO | WO 2006126663 A1 | 11/2006 |
| WO | WO 2007108071 A1 | 9/2007  |
| WO | WO 2010068696    | 6/2010  |
| WO | WO 2011057741 A1 | 5/2011  |

OTHER PUBLICATIONS

Smith et al., "Mechanism of the attenuation of proteolysis-inducing factor stimulated protein degradation in muscle by beta-hydroxy-beta-methylbutyrate", "Cancer Research", Dec. 1, 2004, pp. 8731-8735, vol. 64.
Sousa et al., "Calcium b-hydroxy-b-methylbutyrate. Potential role as a phosphate binder in uremia", "Nephron", 1996, pp. 391-394, vol. 72, Publisher: KARGER.
Sprague et al., "A selective phosphodiesterase 3 inhibitor rescues low PO2-induced ATP release from erythrocytes of humans with type 2 diabetes: implication for vascular control", "American Journal of Physiology Heart and Circulatory Physiology", 2011, pp. H2466-H2472, vol. 301.
Synnestvedt et al., "Ecto-5'-nucleotidase (CD73) regulation by hypoxia-inducible factor-1 mediates permeability changes in intestinal epithelia", "J. Clin. Invest.", 2002, pp. 993-1002, vol. 110.
Thomson et al., "Effects of nine weeks of beta-hydroxy-beta-methylbutyrate supplementation on strength and body composition in resistance trained men", "Journal of Strenth and Conditioning Research", 2009, pp. 827-835, vol. 23.
Alain Trautmann, "Extracellular ATP in the immune system: more than just a 'danger signal'", "Science Signaling", Feb. 3, 2009, vol. 2, No. 56.
Van Someren et al., "Supplementation with beta-hydroxy-beta-methylbutyrate (HMB) and alpha-ketoisocaproic acid (KIC) reduces signs and symptoms of exercise-induced muscle damage in man", "International Journal of Sport Nutrition and Exercise Metabolism", 2005, pp. 413-424, vol. 15.
Wilkinson et al., "Effects of Leucine and its metabolite, beta-hydroxy-beta-methylbutyrate (HMB) on human skeletal muscle protein metabolism", "The Journal of Physiology", 2013, pp. 2911-2923, vol. 591, No. 11.
Wilson et al., "-Hydroxy--Methylbutyrate Free Acid Reduces Markers of Exercise Induced Muscle Damage and Improves Recovery in Resistance Trained Men", "British Journal of Nutrition", 2013, pp. 538-544, vol. 110.
Wilson et al., "Effects of Leucine and its metabolite, beta-hydroxy-beta-methylbutyrate (HMB) on human skeletal muscle protein metabolism", "Nutrition & Metabolism", Jan. 3, 2008, pp. 1-17, vol. 5, No. 1.
Wilson et al., "Effects of beta-hydroxy-beta-methylbutyrate (HMB) on exercise performance and body composition across varying levels of age, sex, and training experience: A review", "The Journal of Strength and Conditioning Research", Mar. 2013, pp. 854-859, vol. 27, No. 3.
Yajima et al., "Inhibitory, facilitatory, and excitatory effects of ATP and purinergic receptor agonists on the activity of rat cutaneous nociceptors in vitro", "Neuroscience Research", 2005, pp. 405-416, vol. 51.
Gennady Yegutkin, "Nucleotide- and nucleoside-converting ectoenzymes: Important modulators of purinergic signalling cascade", "Biochim. Biophys.", 2008, pp. 673-694, vol. 1783.
Agteresch et al., "Adenosine triphosphate: established and potential clinical applications", "Drugs", 1999, pp. 211-232, vol. 58.
Arts et al., "Adenosine 5' -triphosphate (ATP) supplements are not orally bioavailable: a randomized, placebocontrolled cross-over trial in healthy humans", "Journal of the International Society of Sports Nutrition", 2012, pp. 19 vol. 9.

(Continued)

*Primary Examiner* — Traviss C McIntosh, III
(74) *Attorney, Agent, or Firm* — Davis, Brown, Koehn, Shors & Roberts, P.C.; Matthew W. Coryell

(57) ABSTRACT

The present invention provides a composition comprising HMB and ATP. Methods of administering HMB and ATP to an animal are also described. HMB and ATP are administered to increase power and strength. The combination of HMB and ATP together has a synergistic effect, which results in a surprising and unexpected level of improvement in power and strength. HMB and ATP are also administered to increase lean body mass and muscle hypertrophy and to prevent typical declines in performance that are characteristic of overreaching.

18 Claims, 7 Drawing Sheets

(56) References Cited

OTHER PUBLICATIONS

Barnes et al., "Arterial stiffening following eccentric exercise-induced muscle damage", "Journal of Applied Physiology", 2010, pp. 1102-1108, vol. 109.

Burnstock et al., "Purinergic signaling in healthy and diseased skin", "The Society for Investigative Dermatology", 2012, pp. 526-546, vol. 132.

Clark et al., "Nutritional treatment for acquired immunodeficiency virus-associated wasting using b-hydroxy-b-methylbutyrate, glutamine and arginine", "Journal of Parenteral and Enteral Nutrition", May 1, 2000, pp. 133-139, vol. 24, No. 3.

Coolen et al., "Oral bioavailability of ATP after prolonged administration", "British Journal of Nutrition", 2011, pp. 357-366, vol. 105.

Cormie et al., "Developing maximal neuromuscular power: Part 1—biological basis of maximal power production", "Sports Medicine", 2011, pp. 17-38, vol. 41.

Cormie et al., "Developing maximal neuromuscular power: part 2—training considerations for improving maximal power production.", "Sports Medicine", 2011, pp. 17-38, vol. 41.

Dufour et al., "Erythrocyte-dependent regulation of human skeletal muscle blood flow: role of varied oxyhemoglobin and exercise on nitrite, S-nitrosohemoglobin, and ATP", "American Journal of Physiology Heart and Circulatory Physiology", 2010, pp. H1936-H1946, vol. 299.

Eley et al., "Attenuation of depression of muscle protein synthesis induced by lipopolysaccharide, tumor necrosis factor and angiotensin II by b-hydroxy-b-methylbutyrate", "Am J Physiol Endocrinol Metab", Oct. 14, 2008, pp. E1409-E1416, vol. 295.

Eley et al., "Mechanism of Attenuation of Muscle Protein Degradation Induced by Tumor Necrosis Factor Alpha and Angiotensin II by beta-Hydroxy-beta-methylbutyrate", "Am J Physiol Endocrinol", Oct. 7, 2008, vol. 295.

Eley et al., "Signaling pathways initiated by b-hydroxy-b-methylbutyrate to attenuate the depression of protein synthesis in skeletal muscle in response to cachectic stimuli", "Am J Physiol Endocrinol Metab", Jul. 3, 2007, pp. E923-E931, vol. 293.

Ellis et al., "What is the Efficiency of ATP Signaling from Erythrocytes to Regulate Distribution of O(2) Supply within the Microvasculature? Microcirculation", "Microcirculation", Jul. 1, 2012, pp. 440-450, vol. 19, No. 5.

Eubanks et al., "Reversal of cancer-related wasting using oral supplementation with a combination of b-hydroxy-b-methylbutyrate, arginine, and glutamin", "The American Journal of Surgery", Jan. 10, 2002, pp. 471-479, vol. 183.

Fuller et al., "Free acid gel form of beta-hydroxy-beta-methylbutyrate (HMB) improves HMB clearance from plasma in human subjects compared with the calcium HMB salt", "British Journal of Nutrition", 2011, pp. 367-372, vol. 105.

Fuller et al., "Vitamin D status affects strength gains in older adults supplemented with a combination of b-hydroxy-b-methylbutyrate, arginine and lysine: A cohort study", "Journal of Parenteral and Enteral Nutrition", Nov. 3, 2011, pp. 757-762, vol. 35.

Gallagher et al., "b-Hydroxy-b-methylbutyrate ingestion, Part I: Effects on strength and fat free mas", "Official Journal of the American College of Sports Medicine", Mar. 1, 2000, pp. 2109-2115, vol. 32, No. 12.

Gaspari Nutrition—Sizeon, "http://www.gnpd.com/sinatra/recordpage/599558/from_search/SSFK6s8K8V/?page=1", 2006.

Gergs et al., "A positive inotropic effect of ATP in the human cardiac atrium", "American Journal of Physiol Heart Circ Physiol", Feb. 8, 2008, pp. H1716-H1723, vol. 294.

Gergs et al., "A positive inotropic effect of adenosine in cardiac preparations of right atria from diseased human hearts", "Naunyn Schmiedebergs Arch Pharmacol", 2009, pp. 533-540, vol. 379.

Gilbert et al., "Changes in the force development characteristics of muscle following repeated maximum force and power exercise", "Ergonomics", 2005, pp. 1576-1584, vol. 48.

Jose Gonzalez-Alonso, "ATP as a mediator of erythrocyte-dependent regulation of skeletal muscle blood flow and oxygen delivery in humans", "The Journal of Physiology", 2012, pp. 5001-5013, vol. 590.

Gonzalez-Alonso et al., "Erythrocytes and the regulation of human skeletal muscle blood flow and oxygen delivery: role of erythrocyte count and oxygenation state of haemoglobin", "The Journal of Physiology", 2006, pp. 295-305, vol. 572.

Gonzalez-Alonso et al., "Haemodynamic responses to exercise, ATP infusion and thigh compression in humans: insight into the role of muscle mechanisms on cardiovascular function", "The Journal of Physiology", 2008, pp. 2405-2417, vol. 586.

Halson et al., "Does overtraining exist?", "Sports Medicine", 2004, pp. 967-981, vol. 34, No. 14.

Heinonen et al., "Effects of adenosine, exercise, and moderate acute hypoxia on energy substrate utilization of human skeletal muscle", "Am. J. Physiol Regul. Integr. Comp. Physiol.", 2012, pp. R385-R390, vol. 302.

Hung et al., "Effect of [beta]-hydroxy-[beta]-methylbutyrate Supplementation During Energy Restriction in Female Judo Athletes", "Journal of Exercise Science and Fitness", 2010, pp. 50-53, vol. 8.

Jordan et al., "Effects of oral ATP supplementation on anaerobic power and muscular strength", "Medicine & Science in Sports and Exercise", 2004, pp. 383-990, vol. 36.

Jowko et al., "Creatine and beta-hydroxy-beta-methylbutyrate (HMB) additively increase lean body mass and muscle strength during a weight-training program", "Nutrition", 2001, pp. 558-566, vol. 17.

Khakh et al., "ATP receptor-mediated enhancement of fast excitatory neurotransmitter release in the brain", "Molecular Pharmacology", 1998, pp. 372-378, vol. 54.

Kichenin et al., "Cardiovascular and pulmonary response to oral administration of ATP in rabbits", "J Appl Physiol", 2000, pp. 1962-1968, vol. 88.

Knitter et al., "Effects of b-hydroxy-b-methylbutyrate on muscle damage following a prolonged run", "J. Appl. Physiol.", 2000, pp. 1340-1344, vol. 89, No. 4.

Kraemer et al., "Effects of Amino Acids Supplement on Physiological Adaptations to Resistance Training", "Medicine & Science in Sports & Exercise", 2009, pp. 1111-1121, vol. 41.

Kraemer et al., "Fundamentals of resistance training: progression and exercise prescription", "Physical Fitness and Performance", 2004, pp. 674-688, vol. 36.

Kushmerick et al., "Energetics of muscle contraction: the whole is less than the sum of its parts", "Biochemical Society", 2002, pp. 227-231, vol. 30.

Laurent et al., "Nonlinear periodization maximizes strength gains in split resistance training routines", "Journal of Strength and Conditioning Research", 2011, pp. 620-628, vol. 25, No. 3.

Monteiro et al., "Nonlinear Periodization Maximizes Strength Gains in Split Resistance Training Routines", "Journal of Strength & Conditioning Research", 2009, pp. 1321-1326, vol. 23.

Metabolic Technologies, Inc., "The Effects of HMB, ATP and HMB Plus ATP on Muscle Mass, Strength and Power in Resistance Trained Athletes", "ClinicalTrials.gov", 2012.

Niseen et al., "Effect of dietary supplements on lean mass and strength gains with resistance exercise: a meta-analysis", "J Appl Physiol", Oct. 25, 2002, pp. 651-2003, vol. 94.

Nissen et al., "Effect of the leucine metabolite b-hydroxy b-methylbutyrate on muscle metabolism during resistance-exercise training", 1996, pp. 2095-2104, vol. 81, No. 5.

Nyberg et al., "Interstitial and plasma adenosine stimulate nitric oxide and prostacyclin formation in human skeletal muscle.", "Hypertenstion", 2010, pp. 1102-1108, vol. 56.

Jowko et al., "Creatine and b-hydroxy-b-methylbutyrate (HMB) additively increases lean body mass and muscle strength during a weight training program", "Nutrition", 2001, pp. 558-566, vol. 17.

Ostaszewski et al., "The leucine metabolite 3-hydroxy-3-methylbutyrate (HMB) modifies protein turnover in muscles of the laboratory rats and domestic chicken in vitro", "J. Anim. Physiol. a. Anim. Nutr.", 2000, pp. 1-8, vol. 84qq.

Panton et al., "Nutritional supplementation of the leucine metabolite b-hydroxy b-methylbutyrate (HMB) during resistance training", "Nutrition", Nov. 9, 2000, pp. 734-739, vol. 16, No. 9.

(56) References Cited

OTHER PUBLICATIONS

Rathmacher et al., "Adenosine-5'-triphosphate (ATP) supplementation improves low peak muscle torque and torque fatigue during repeated high intensity exercise sets", "Journal of the International Society of Sports Nutrition", 2012, pp. 48, vol. 9.

Rathmacher et al., "Gas chromatographic-mass spectrometric analysis of stable isotopes of 3-methylhistidine in biological fluids: application to plasma kinetics in vivo", "Biol. Mass Spectrom", 1992, pp. 560-566, vol. 21.

Robbins et al., "Effect of loading on enhancement of power performance over three consecutive trials", "Journal of Strength and Conditioning Research", 2005, pp. 898-902, vol. 19.

Russell et al., "Mechanism of attenuation by beta-hydroxy-beta-methylbutyrate of muscle protein degradation induced by lipopolysaccharide", "Mol CEll Biochem", 2009, pp. 171-179, vol. 330.

Sawynok et al., "The Role of Purines in Nociception", "Neuroscience", 1989, pp. 557-569, vol. 32, No. 3.

Smith et al., "Attenuation of proteasome-induced proteolysis in skeletal muscle by b-hydroxy-b-methylbutyrate in cancer-induced muscle loss", "Cancer Research", Jan. 1, 2005, pp. 277-283, vol. 65.

\* cited by examiner

Squat Strength, 1-RM Change in 12 Weeks

Main Effects: HMB p=0.0001; ATP, p=0.005; HMB*ATP, p=0.11

Bench Press Strength, 1-RM Change from 4 to 8 Weeks

Main Effects: HMB p=0.004; ATP, p=0.01; HMB*ATP, p=0.04

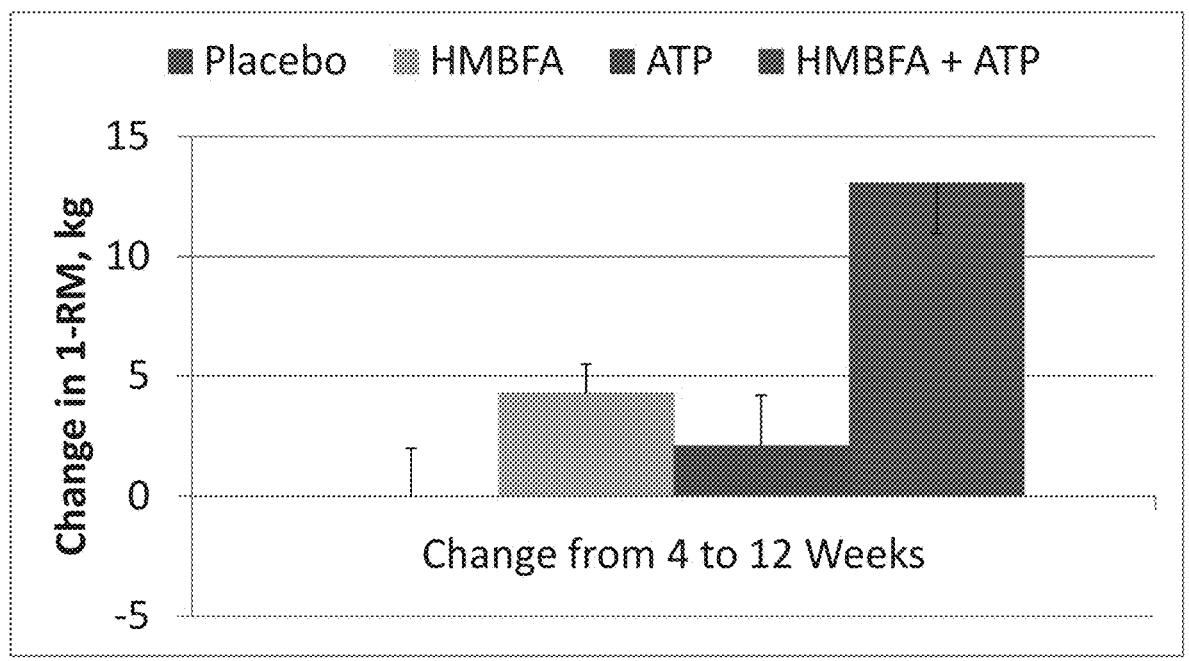

COMPOSITION OF HMB AND ATP AND METHODS OF USE

This application is a continuation of U.S. patent application Ser. No. 14/023,162 filed Sep. 10, 2013, which claims the benefit of U.S. Patent Application Ser. No. 61/698,919, filed Sep. 10, 2012, which is incorporated herein in its entirety by this reference.

BACKGROUND OF THE INVENTION

Field

The present invention relates to a composition comprising β-hydroxy-β-methylbutyrate (HMB) and adenosine-5'-triphosphate (ATP), and methods of using a combination of HMB and ATP to improve strength and power, improve muscle mass and prevent or lessen typical declines in performance characteristic of overreaching.

Background

HMB

The only product of leucine metabolism is ketoisocaproate (KIC). A minor product of KIC metabolism is β-hydroxy-β-methylbutyrate (HMB). HMB has been found to be useful within the context of a variety of applications. Specifically, in U.S. Pat. No. 5,360,613 (Nissen), HMB is described as useful for reducing blood levels of total cholesterol and low-density lipoprotein cholesterol. In U.S. Pat. No. 5,348,979 (Nissen et al.), HMB is described as useful for promoting nitrogen retention in humans. U.S. Pat. No. 5,028,440 (Nissen) discusses the usefulness of HMB to increase lean tissue development in animals. Also, in U.S. Pat. No. 4,992,470 (Nissen), HMB is described as effective in enhancing the immune response of mammals. U.S. Pat. No. 6,031,000 (Nissen et al.) describes use of HMB and at least one amino acid to treat disease-associated wasting.

HMB is an active metabolite of the amino acid leucine. The use of HMB to suppress proteolysis originates from the observations that leucine has protein-sparing characteristics. The essential amino acid leucine can either be used for protein synthesis or transaminated to the α-ketoacid (α-ketoisocaproate, KIC). In one pathway, KIC can be oxidized to HMB. Approximately 5% of leucine oxidation proceeds via the second pathway. HMB is superior to leucine in enhancing muscle mass and strength. The optimal effects of HMB can be achieved at 3.0 grams per day, or 0.038 g/kg of body weight per day, while those of leucine require over 30.0 grams per day.

Once produced or ingested, HMB appears to have two fates. The first fate is simple excretion in urine. After HMB is fed, urine concentrations increase, resulting in an approximate 20-50% loss of HMB to urine. Another fate relates to the activation of HMB to HMB-CoA. Once converted to HMB-CoA, further metabolism may occur, either dehydration of HMB-CoA to MC-CoA, or a direct conversion of HMB-CoA to HMG-CoA, which provides substrates for intracellular cholesterol synthesis. Several studies have shown that HMB is incorporated into the cholesterol synthetic pathway and could be a source for new cell membranes that are used for the regeneration of damaged cell membranes. Human studies have shown that muscle damage following intense exercise, measured by elevated plasma CPK (creatine phosphokinase), is reduced with HMB supplementation within the first 48 hrs. The protective effect of HMB lasts up to three weeks with continued daily use.

Numerous studies have shown an effective dose of HMB to be 3.0 grams per day as CaHMB (calcium HMB) (~38 mg/kg body weight-day$^{-1}$). This dosage increases muscle mass and strength gains associated with resistance training, while minimizing muscle damage associated with strenuous exercise (34) (4, 23, 26). HMB has been tested for safety, showing no side effects in healthy young or old adults. HMB in combination with L-arginine and L-glutamine has also been shown to be safe when supplemented to AIDS and cancer patients.

Recently, HMB free acid, a new delivery form of HMB, has been developed. This new delivery form has been shown to be absorbed quicker and have greater tissue clearance than CaHMB. The new delivery form is described in U.S. Patent Publication Serial No. 20120053240 which is herein incorporated by reference in its entirety.

ATP

Adenosine-5'-triphosphate (ATP) has long been known as the chemical energy source for tissues including muscle (19). Intracellular ATP concentrations (1-10 mM) are quite high in contrast to extracellular concentrations (10-100 nM) and therefore release of ATP from cells such as erythrocytes and muscle is strictly controlled. More recently extracellular effects of ATP, acting through purinergic receptors found in most cell types, have been elicited (20). Several extracellular physiological functions of ATP have been described including vasodilation (21), reduced pain perception (22), and as a neurotransmission cotransmitter (23, 24). Importantly, small and transient increases in vascular ATP in muscle can cause vasodilation and an increase in blood flow to the muscle (25). Therefore, if ATP increases blood flow to muscle, especially during periods of strenuous resistance training, substrate availability would be improved and removal of metabolic waste products would be better facilitated. Ellis et al recently reviewed the studies supporting the role of ATP in increasing muscle blood flow through purinergic signaling and neurotransmission (25).

ATP has been shown to have an inotrophic effect ATP on cardiac muscle (26, 27). Another study supporting systemic effects of ATP demonstrated that oral administration of ATP to rabbits for 14 days resulted in a reduction in peripheral vascular resistance, improvement of cardiac output, reduction of lung resistance, and increased arterial $PaO_2$ (28).

Adenosine, resulting from the degradation of ATP, may also act as a signaling agent through purinergic receptors (29) or may be degraded by adenosine deaminase (30). Adenosine acting through purinergic receptors can essentially mimic the effects of ATP (29). Adenosine infusion into muscle results in increased nitric oxide formation and similar vascular effects as seen with ATP infusion (31).

Fatigue resistance in repeated high intensity bouts of exercise is a much sought after attribute in athletics. This is true for both augmentation of training volume, as well as sustained force and power output in intermittent sports such as hockey. During fatiguing contractions acute adaptations in blood flow occur to stave off declines in force generating capacity (40, 45). There is a tight coupling between oxygen demand in skeletal muscle and increases in blood flow (45). Research suggests that it is red blood cells that regulate this response by acting as "oxygen sensors" (45). ATP is carried in red blood cells and when oxygen is low in a working muscle region, the red blood cell deforms resulting in a cascade of events which lead to ATP release and binding to endothelial cells in smooth muscle (43). Binding results in smooth muscle relaxation and subsequent increases in blood flow, nutrient and oxygen delivery (43). Specifically, extracellular ATP directly promotes the increased synthesis and release of nitric oxide (NO) and prostacyclin (PGI$_2$) within skeletal muscle and therefore directly affects tissue vasodilation and blood flow (31). This is supported by research suggesting increased vasodilation and blood flow in response to intra-arterial infusion (47) and exogenous administration of ATP. These changes in blood flow likely lead to an increased substrate pool for skeletal muscle by virtue of increased glucose and O$_2$ uptake (42). The outcome is maintenance of energy status in the cell under fatiguing contractions. (54, 56)

The physiological effects of ATP have led researchers to investigate the efficacy of oral supplementation of ATP (24). Jordan et al. (32) demonstrated that 225 mg per day of enteric-coated ATP supplementation for 15 days resulted in increased total bench press lifting volume (i.e. sets•repetitions•load) as well as within-group set-one repetitions to failure. More recently, Rathmacher et al. (52) found that 15 days of 400 mg per day of ATP supplementation increased minimum peak torque in set two of a knee extensor bout. Collectively the results discussed indicate that ATP supplementation maintains performance and increases training volume under high fatiguing conditions. However, greater fatigue increases recovery demands between training sessions.

Current evidence suggests that HMB acts by speeding regenerative capacity of skeletal muscle following high intensity or prolonged exercise (3). When training and/or diet are controlled, HMB can lower indices of skeletal muscle damage and protein breakdown in a dose-dependent fashion (50, 3, 2). Recently, HMB in a free acid form (HMB-FA) has been developed with improved bioavailability (18). Initial studies have shown that this form of HMB supplementation results in approximately double the plasma levels of HMB in about one-quarter the time after administration when compared with the presently available form, calcium HMB.

Further, HMB-FA given 30 minutes prior to an acute bout of high volume resistance training was able to attenuate indices of muscle damage and improve perceived recovery in resistance trained athletes (61). Moreover acute ingestion of 2.4 grams of HMB-FA increases skeletal muscle protein synthesis and decreases protein breakdown by +70% and −56% respectively (58).

A need exists for a composition and methods to increase strength and power and improve muscle mass. In addition, a need exists for a composition that prevents or lessens the typical decay seen in performance following an overreaching cycle. The present invention comprises a composition and methods of using a combination of ATP and HMB that results in these improvements.

SUMMARY OF THE INVENTION

One object of the present invention is to provide a composition for use in increasing strength and power.

A further object of the present invention is to provide a composition for use in improving muscle mass.

Another object of the present invention is to provide methods of administering a composition for increasing strength and power.

An additional object of the present invention is to provide methods of administering a composition for improving muscle mass.

Another object of the present invention is to provide a composition for use in preventing or lessening decay seen in performance following an overreaching cycle.

These and other objects of the present invention will become apparent to those skilled in the art upon reference to the following specification, drawings, and claims.

The present invention intends to overcome the difficulties encountered heretofore. To that end, a composition comprising HMB and ATP is provided. The composition is administered to an animal in need thereof. All methods comprise administering to the animal HMB and ATP.

BRIEF DESCRIPTION OF THE FIGURES

FIGS. 3a-c show changes in squat strength and bench press strength.

DETAILED DESCRIPTION OF THE INVENTION

Figure 1:
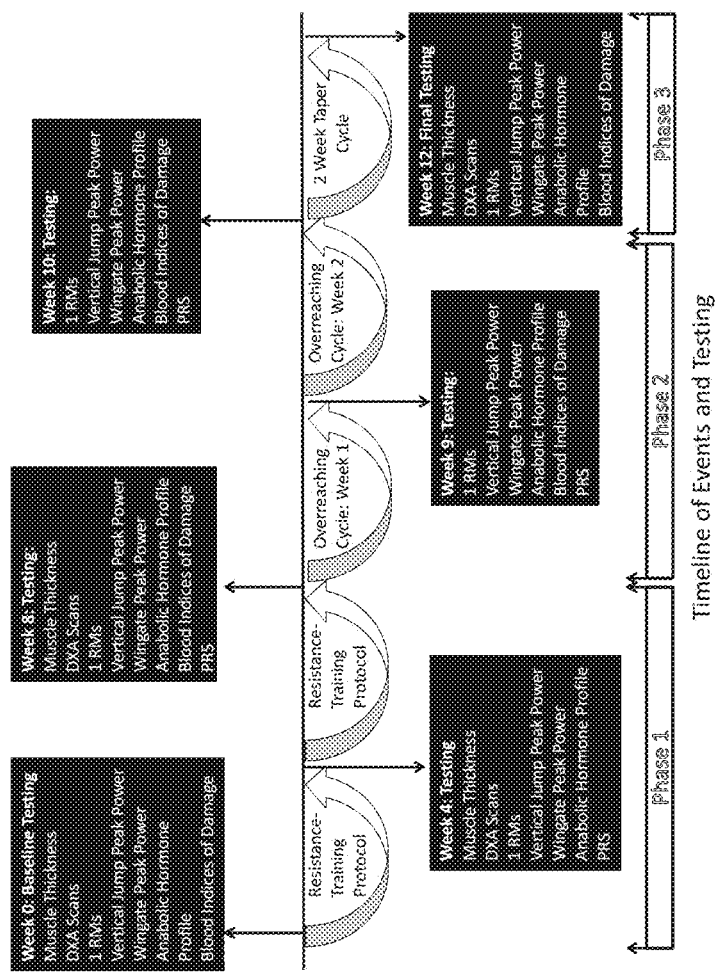
FIG. 1 is a schemata of phases of the training program listing variables and the time points of measurement throughout the study.

It has been surprisingly and unexpectedly discovered that a combination of HMB and ATP results in greater increases in strength, power and muscle mass than use of either HMB or ATP alone. The present invention comprises a combination of HMB and ATP that has a synergistic effect and increases strength and power. The present invention also comprises a combination of HMB and ATP that has the unexpected and surprising results of improving muscle mass. The present invention also comprises a combination of HMB and ATP that has the unexpected and surprising result of preventing or lessening typical decay seen in performance following an overreaching cycle. The combination of HMB and ATP results in significant enhancements.

This combination can be used on all age groups seeking increases in strength and power, increases in muscle mass, and prevention or lessening of typical decay seen in performance following an overreaching cycle.

In view of the above, in one embodiment the present invention provides a composition comprising HMB and ATP.

HMB

β-hydroxy-β-methylbutyric acid, or β-hydroxy-isovaleric acid, can be represented in its free acid form as $(CH_3)_2(OH)CCH_2COOH$. The term "HMB" refers to the compound having the foregoing chemical formula, in both its free acid and salt forms, and derivatives thereof. While any form of HMB can be used within the context of the present invention, preferably HMB is selected from the group comprising a free acid, a salt, an ester, and a lactone. HMB esters include methyl and ethyl esters. HMB lactones include isovalaryl lactone. HMB salts include sodium salt, potassium salt, chromium salt, calcium salt, magnesium salt, alkali metal salts, and earth metal salts.

Methods for producing HMB and its derivatives are well-known in the art. For example, HMB can be synthesized by oxidation of diacetone alcohol. One suitable procedure is described by Coffman et al., *J. Am. Chem. Soc.* 80: 2882-2887 (1958). As described therein, HMB is synthesized by an alkaline sodium hypochlorite oxidation of diacetone alcohol. The product is recovered in free acid form, which can be converted to a salt. For example, HMB can be prepared as its calcium salt by a procedure similar to that of Coffman et al. (1958) in which the free acid of HMB is neutralized with calcium hydroxide and recovered by crystallization from an aqueous ethanol solution. The calcium salt of HMB is commercially available from Metabolic Technologies, Ames, Iowa.

Calcium β-hydroxy-β-methylbutyrate (HMB) Supplementation

More than 2 decades ago, the calcium salt of HMB was developed as a nutritional supplement for humans. Numerous studies have shown that CaHMB supplementation improves muscle mass and strength gains in conjunction with resistance-exercise training, and attenuates loss of muscle mass in conditions such as cancer and AIDS (1-5). Nissen and Sharp performed a meta-analysis of supplements used in conjunction with resistance training and found that HMB was one of only two supplements that had clinical studies showing significant increases in strength and lean mass with resistance training (1). Studies have shown that 38 mg of CaHMB per kg of body weight appears to be an efficacious dosage for an average person (6).

In addition to strength and muscle mass gains, CaHMB supplementation also decreases indicators of muscle damage and protein degradation. Human studies have shown that muscle damage following intense exercise, measured by elevated plasma CPK (creatine phosphokinase), is reduced with HMB supplementation. The protective effect of HMB has been shown to manifest itself for at least three weeks with continued daily use (6-8) In vitro studies in isolated rat muscle show that HMB is a potent inhibitor of muscle proteolysis (9) especially during periods of stress. These findings have been confirmed in humans; for example, HMB inhibits muscle proteolysis in subjects engaging in resistance training (3).

The molecular mechanisms by which HMB decreases protein breakdown and increases protein synthesis have been reported (10, 11). Eley et al conducted in vitro studies which have shown that HMB stimulates protein synthesis through mTOR phosphorylation (11, 12). Other studies have shown HMB decreases proteolysis through attenuation of the induction of the ubiquitin-proteosome proteolytic pathway when muscle protein catabolism is stimulated by proteolysis inducing factor (PIF), lipopolysaccharide (LPS), and angiotension II (10, 13, 14). Still other studies have demonstrated that HMB also attenuates the activation of caspases-3 and -8 proteases (15). Taken together these studies indicate that HMB supplementation results in increased lean mass and the accompanying strength gains through a combination of decreased proteolysis and increased protein synthesis.

HMB Free Acid Form

In most instances, the HMB utilized in clinical studies and marketed as an ergogenic aid has been in the calcium salt form (3, 16). Recent advances have allowed the HMB to be manufactured in a free acid form for use as a nutritional supplement. Recently, a new free acid form of HMB was developed, which was shown to be more rapidly absorbed than CaHMB, resulting in quicker and higher peak serum HMB levels and improved serum clearance to the tissues (18).

HMB free acid may therefore be a more efficacious method of administering HMB than the calcium salt form, particularly when administered directly preceding intense exercise. HMB free acid initiated 30 min prior to an acute bout of exercise was more efficacious in attenuating muscle damage and ameliorating inflammatory response than CaHMB. One of ordinary skill in the art, however, will recognize that this current invention encompasses HMB in any form.

HMB in any form may be incorporated into the delivery and/or administration form in a fashion so as to result in a typical dosage range of about 0.5 grams HMB to about 30 grams HMB.

Adenosine-5'-triphosphate (ATP)

Supplementation with adenosine-5'-triphosphate (ATP) has been used to elevate extracellular ATP levels. Studies have failed to show consistent positive effects of ATP to improve strength or power when combined with resistance-training exercise; however, small and transient increases in systemic ATP have been shown to increase blood flow in muscle tissue.

Oral administration of ATP is usually in the form of Adenosine-5'-Triphospate Disodium. In the present invention, Adenosine-5'-Triphosphate Disodium or any form of ATP or adenosine suitable for oral administration may be combined with any of the known coatings suitable for imparting enteric properties in granular form.

ATP may be incorporated into the delivery and/or administration form in a fashion so as to result in a typical dosage range of about 10 mg to about 80 grams, though more or less may be desirable depending on the application and other ingredients.

The composition of HMB and ATP is administered to an animal in any suitable manner. Acceptable forms include, but are not limited to, solids, such as tablets or capsules, and liquids, such as enteral or intravenous solutions. Also, the composition can be administered utilizing any pharmaceutically acceptable carrier. Pharmaceutically acceptable carriers are well known in the art and examples of such carriers include various starches and saline solutions. In the preferred embodiment, the composition is administered in an edible form. In addition, an effective dosage range may be administered in divided dosages, such as two to three times per day.

ATP and HMB Combination

Any suitable dose of HMB can be used within the context of the present invention. Methods of calculating proper doses are well known in the art. The dosage amount of HMB can be expressed in terms of corresponding mole amount of Ca-HMB. The dosage range within which HMB may be administered orally or intravenously is within the range from 0.01 to 0.5 grams HMB (Ca-HMB) per kilogram of body weight per 24 hours. For adults, assuming body weights of from about 100 to 200 lbs., the dosage amount orally or intravenously of HMB (Ca-HMB basis) can range from 0.5 to 30 grams per subject per 24 hours.

ATP is present in the composition in any form. A range of ATP in the present invention includes ATP in the amount of around 10 milligrams to around 80 grams.

When the composition is administered orally in an edible form, the composition is preferably in the form of a dietary supplement, foodstuff or pharmaceutical medium, more preferably in the form of a dietary supplement or foodstuff. Any suitable dietary supplement or foodstuff comprising the composition can be utilized within the context of the present invention. One of ordinary skill in the art will understand that the composition, regardless of the form (such as a dietary supplement, foodstuff or a pharmaceutical medium), may include amino acids, proteins, peptides, carbohydrates, fats, sugars, minerals and/or trace elements.

In order to prepare the composition as a dietary supplement or foodstuff, the composition will normally be combined or mixed in such a way that the composition is substantially uniformly distributed in the dietary supplement or foodstuff. Alternatively, the composition can be dissolved in a liquid, such as water.

The composition of the dietary supplement may be a powder, a gel, a liquid or may be tabulated or encapsulated.

Although any suitable pharmaceutical medium comprising the composition can be utilized within the context of the present invention, preferably, the composition is combined with a suitable pharmaceutical carrier, such as dextrose or sucrose.

Furthermore, the composition of the pharmaceutical medium can be intravenously administered in any suitable manner. For administration via intravenous infusion, the composition is preferably in a water-soluble non-toxic form. Intravenous administration is particularly suitable for hospitalized patients that are undergoing intravenous (IV) therapy. For example, the composition can be dissolved in an IV solution (e.g., a saline or glucose solution) being administered to the patient. Also, the composition can be added to nutritional IV solutions, which may include amino acids, peptides, proteins and/or lipids. The amounts of the composition to be administered intravenously can be similar to levels used in oral administration. Intravenous infusion may be more controlled and accurate than oral administration.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period, or, alternatively, multiple doses can be administered over an extended time period). The combination of HMB and ATP can be administered over an extended period of time, such as weeks, months or years.

It will be understood by one of ordinary skill in the art that HMB and ATP do not have to be administered in the same composition to perform the claimed methods. Stated another way, separate capsules, pills, mixtures, etc. of ATP and of HMB may be administered to a subject to carry out the claimed methods.

Any suitable dose of HMB can be used within the context of the present invention. Methods of calculating proper doses are well known in the art. Likewise, any suitable dose of ATP can be used within the context of the present invention. Methods of calculating proper doses are well known in the art.

In general, an amount of HMB and ATP in the levels sufficient to increase strength and power is described. Both HMB free acid alone and HMB free acid plus ATP supplementation increased strength and power gains greater than those observed with placebo supplementation ($p<0.001$, treatment*time). Surprisingly, post hoc analysis showed that HMB plus ATP supplementation significantly further improved strength and power gains over those for HMB supplementation alone ($p<0.05$). The following experimental examples indicate that HMB does have a positive effect on strength, power, and muscle mass and reduces muscle damage while aiding in recovery. Surprisingly, the combination of HMB plus ATP resulted in even greater improvement in strength and power compared to HMB alone and these effects are synergistic. Additionally, the HMB-ATP combination also demonstrated surprising and unexpected effects on muscle mass and declines in performance that are characteristic of overreaching.

EXPERIMENTAL EXAMPLES

The following examples will illustrate the invention in further detail. It will be readily understood that the composition of the present invention, as generally described and illustrated in the Examples herein, could be synthesized in a variety of formulations and dosage forms. Thus, the following more detailed description of the presently preferred embodiments of the methods, formulations and compositions of the present invention are not intended to limit the scope of the invention, as claimed, but it is merely representative of the presently preferred embodiments of the invention.

In the examples, overreaching is an increase in training volume and/or intensity of exercise resulting in performance decrements. Recovery from this condition often requires a few days to a week or more. Many structured training programs utilize phases of overreaching to induce an adaptive response.

Lean body mass (LBM) and hypertrophy increases are used as indicators of improving muscle mass.

Study Design

The current study was a randomized, double-blind, placebo- and diet-controlled experiment consisting of 12 weeks of periodized resistance training. The training protocol was divided into 3 phases (Tables 1, 2, and 3). Phase 1 consisted of a non-linear periodized resistance training program (3 times per week) modified from Kraemer et al. (36) (Table 1).

TABLE 1

Phase 1 of the training cycle (Daily Undulating Periodization).

| Monday | Wednesday | Friday |
|---|---|---|
| Squat | Squat | Squat (5 sets) |
| Barbell Bench Press | Bench | Barbell Bench Press (5 sets) |
| Deadlifts | Deadlift | Deadlifts |
| Pull Ups/Dips (Superset) |  | Pull Ups/Dumbbell Shoulder Press (Superset) |
| Bent Over Row |  | Bent Over Row |
| Dumbbell Shoulder Press |  | Dumbbell Shoulder Press |
| Barbell Curl/Triceps Extension (Superset) |  | Barbell Curls/Triceps Extension (Superset) |
| Repetition, Set Schema | Repetition, Set Schema | Repetition, Set Schema |
| 3 sets | 5 sets | 3 sets *(Squat and Bench = 5 sets) |
| 8-12 RM loads | 5 maximal intended velocity repetitions | 3-5 RM loads |
| 60 seconds timed rest | 180 seconds timed rest | 240 seconds timed rest |

Phase 2 (Table 2) consisted of a two week overreaching cycle.

TABLE 2

Phase 2 of the training cycle (Overreaching).

| Monday | Tuesday | Wednesday | Thursday | Friday | Saturday |
|---|---|---|---|---|---|
| Squat | Leg Press | Squat | Leg Press | Squat 1 RM | Wingate and Maximal Power Testing |

TABLE 2-continued

Phase 2 of the training cycle (Overreaching).

| | | | | |
|---|---|---|---|---|
| Barbell Bench Press | Barbell Bench Press | Barbell Bench Press | Barbell Bench Press | Bench Press 1 RM |
| Deadlifts | Military Press | Deadlifts | Military Press | Deadlift 1 RM |
| Pull Ups/Dips (Superset) | Supinated Pull Ups/Dips (Superset) | Pull Ups/Dips (Superset) | Supinated Pull Ups/Dips (Superset) | |
| Bent Over Row Dumbbell Shoulder Press | Bent Over Row Hammer Curls/ Close Grip Bench (Superset) | Bent Over Row Dumbbell Shoulder Press | Bent Over Row Hammer Curls/ Close Grip Bench (Superset) | |
| Barbell Curl/ Triceps Extension (Superset) | | Barbell Curl/ Triceps Extension (Superset) | | |

| Repetition, Set Schema | Repetition, Set Schema | Repetition, Set Schema | Repetition, Set Schema | Repetition, Set Schema |
|---|---|---|---|---|
| 3 sets | 3 sets | 3 sets | 3 sets | 3 Maximal Attempts (Highest Counted as 1 RM) |
| 8 RM loads | 8 RM loads | 12 RM loads | 12 RM loads | 1 RM load |
| 60 seconds timed rest | 60 seconds timed rest | 60 seconds timed rest | 60 seconds timed rest | 5 minutes timed rest |
| 75% 1 RM | 75% 1 RM | 65% 1 RM | 65% 1 RM | |

Finally, phase 3 consisted of a tapering of the training volume for weeks 11 and 12 (Table 3).

TABLE 3

Phase 3 of the training cycle (Taper).

| Week 11 | | | Week 12 | | |
|---|---|---|---|---|---|
| Monday | Wednesday | Friday | Monday | Wednesday | Friday |
| Squat | Squat (3 sets) | Squat | Squat (3 sets) | Squat | Squat 1 RM |
| Barbell Bench Press | Barbell Bench Press (3 sets) | Barbell Bench Press | Barbell Bench Press (3 sets) | Barbell Bench Press | Bench Press 1 RM |
| Deadlifts | Deadlifts Pull Ups/Dumbbell Shoulder Press (Superset) Bent Over Row Dumbbell Shoulder Press Barbell Curls/ Triceps Extension (Superset) | Deadlifts | Deadlifts Pull Ups/Dumbbell Shoulder Press (Superset) Bent Over Row Dumbbell Shoulder Press Barbell Curls/ Triceps Extension (Superset) | Deadlifts | Deadlift 1 RM |

| Repetition, Set Schema | Repetition, Set Schema | Repetition, Set Schema | Repetition, Set Schema | Repetition, Set Schema | Repetition, Set Schema |
|---|---|---|---|---|---|
| 5 sets | 1 set *(Squat and Bench = 3 sets) | 5 sets | 1 set *(Squat and Bench = 3 sets) | 5 sets | 3 Maximal Attempts (Highest Counted as 1 RM) |
| 5 maximal intended velocity repetitions | 3-5 RM loads | 5 maximal intended velocity repetitions | 3-5 RM loads | 5 maximal intended velocity repetitions | 1 RM load |
| 180 seconds timed rest | 240 seconds timed rest | 180 seconds timed rest | 240 seconds timed rest | 180 seconds timed rest | 5 minutes timed rest |
| 40-60% 1 RM | >90% 1 RM | 40-60% 1 RM | >90% 1 RM | 40-60% 1 RM | |

Muscle mass, body composition, strength, power, resting plasma testosterone, cortisol concentrations, and creatine kinase were examined collectively at the end of weeks 0, 4, 8, 9, 10, and 12 to assess the chronic effects of HMB-ATP; these were also assessed at the end of weeks 9 and 10, corresponding to the mid- and endpoints of the phase 2 overreaching cycle. An overview of the study design is summarized in FIG. 1.

Participants

Forty resistance-trained males aged 23.0±0.9 years with an average squat, bench press, and deadlift of 1.7±0.04, 1.3±0.04 and 2.0±0.05 times their bodyweight were recruited for the study. Subject characteristics are represented in Table 4. Participants could not participate if they were currently taking anti-inflammatory agents, any other performance-enhancing supplement, or if they smoked. Each participant signed an informed consent approved by the University of Tampa Institutional Review Board before participating in the study.

TABLE 4

Subject Descriptors.

| | Treatments | | | |
|---|---|---|---|---|
| | Placebo | HMB-FA | ATP | HMB-FA plus ATP |
| N | 10 | 11 | 11 | 8 |
| Age, y | 23.0 ± 1.2 | 21.3 ± 0.6 | 23.7 ± 0.9 | 21.4 ± 0.3 |
| Body Weight, kg | 87.4 ± 4.3 | 83.1 ± 2.8 | 85.7 ± 1.7 | 81.9 ± 2.1 |
| Height, cm | 180.6 ± 2.3 | 179.0 ± 2.1 | 179.0 ± 1.0 | 177.2 ± 1.3 |
| Body Mass Index | 26.6 ± 0.7 | 25.9 ± 0.7 | 26.7 ± 0.4 | 26.1 ± 0.6 |

Muscle Strength, Power, Body Composition and Skeletal Muscle Hypertrophy Testing After familiarization with procedures, muscle strength was assessed via 1RM testing of the back squat, bench press, and deadlift. Each lift was performed as described by the International Powerlifting Federation rules (44). Body composition (lean body mass, fat mass, and total mass) was determined by dual x-ray absorptiometry (DXA; Lunar Prodigy enCORE 2008, Madison, Wis., U.S.A.). Skeletal muscle hypertrophy was determined via the combined changes in ultrasonography-determined muscle thickness of the vastus lateralis (VL) and vastus intermedius (VI) muscles. The intraclass correlation coefficient (ICC) for the test-retest of muscle thickness measurements was r=0.97.

Muscle power was assessed during maximal cycling (Wingate Test) and jumping movements. During the cycling test, volunteers were instructed to cycle against a predetermined resistance (7.5% of body weight) as fast as possible for 10 seconds (36). The saddle height was adjusted to the individual's height to produce a 5-10° knee flexion while the foot was in the low position of the central void. A standardized verbal stimulus was provided to each participant. Power output was recorded in real time during the 10-second sprint test, by a computer connected to the standard cycle ergometer (Monark model 894e, Vansbro, Sweden). Peak power (PP) was recorded using Monark Anaerobic Wingate Software, Version 1.0 (Monark, Vansbro, Sweden). The ICC of muscle peak power was 0.96.

Measurements of PP were also taken during a vertical jump (VJ) test performed on a multi-component AMTI force platform (Advanced Mechanical Technology, Inc., Watertown, Mass.), interfaced with a personal computer at a sampling rate of 1000 Hz (51). Data acquisition software (LabVIEW, version 7.1; National Instruments Corporation, Austin, Tex.) was used to calculate PP. Peak power was calculated as the peak combination of ground reaction force and peak velocity during the accelerated launch on the platform. The ICC of VJ power was 0.97.

Supplementation, Diet Control, and Exercise Protocol

Prior to the study, participants were randomly assigned to receive either 3 g per day of HMB Free Acid (HMB) (combined with food-grade orange flavors and sweeteners), 400 mg per day of ATP (PEAK ATP®; TSI, Inc.), a combination of both 3 g of HMB and 400 mg per day of ATP, or a placebo (food-grade orange flavors and sweeteners) divided equally into three servings daily with the first serving given 30 minutes prior to exercise and the remaining two servings daily with the mid-day and evening meals. On the non-training days participants were instructed to consume one serving with each of three separate meals. The supplementation was continued daily throughout the training and testing protocols. Each serving was formulated with 1 gram of HMB free acid to account for fill and emptying variation and achieve a minimum effective dosage of 0.800 grams. This dosage would be equivalent to a 1 gram Ca-HMB dosage.

The participants must not have taken any nutritional supplements for at least three months prior to the start of data collection. Two weeks prior to and throughout the study, participants were placed on a diet consisting of 25% protein, 50% carbohydrates, and 25% fat by a registered dietician who specialized in sports nutrition. The participants met as a group with the dietitian, and they were given individual meal plans at the beginning of the study. Diet counselling was continued on an individual basis throughout the study.

All participants performed a high volume resistance training protocol during the 12-week study. The phases of the study and measurements taken are shown in FIG. 1, and the exercise protocols for each phase of the study are shown in Tables 1 to 3. The training was divided into 3 phases, with Phase 1 consisting of daily undulating periodization (weeks 1 to 8), Phase 2 consisting of the overreaching cycle (weeks 9 and 10), and Phase 3 consisting of the taper cycle (weeks 11 and 12).

Resting Blood Draws

All blood draws throughout the study were obtained via venipuncture after a 12-hour fast by a trained phlebotomist. Whole blood was collected and transferred into appropriate tubes for obtaining serum and plasma and centrifuged at 1,500 g for 15 min at 4° C. Resulting serum and plasma were then aliquoted and stored at −80° C. until subsequent analyses.

Biochemical Analysis

Samples were thawed one time and analyzed in duplicate for each analyte. All blood draws were scheduled at the same time of day to negate confounding influences of diurnal hormonal variations. Serum total and free testosterone, cortisol, and C-reactive protein (CRP) were assayed via ELISA kits obtained from Diagnostic Systems Laboratories (Webster, Tex.). All hormones were measured in the same assay on the same day to avoid compounded interassay variance. Intra-assay variance was less than 3% for all analytes. Serum creatine kinase (CK) was measured using colorimetric procedures at 340 nm (Diagnostics Chemicals, Oxford, Conn.). Twenty-four hour urine collections were made and 3-methylhistine was determined by previously described methods (Rathmacher et al 1992 and Wilson et al, 2013).

Perceived Recovery Status Scale

Perceived Recovery Status (PRS) scale was measured at weeks 0, 4, 8, 9, 10, and 12 to assess subjective recovery during the training phases. The PRS scale consists of values between 0-10, with 0-2 being very poorly recovered and with anticipated declines in performance, 4-6 being low to moderately recovered and expected similar performance, and 8-10 representing high perceived recovery with expected increases in performance.

Statistics

A one-way ANOVA model was used to analyze the baseline characteristic data using the Proc GLM procedure in SAS (Version 9.1,SAS Institute, Cary, N.C.)[1] (SAS Institute, Inc. (1985) SAS User's Guide: Statistics, 5th ed. Cary, N.C.: SAS Institute, Inc.). The main effect of treatment (Trt) was included in the model. Muscle strength and power, body composition, muscle damage, hormonal status, and perceived recovery score (PRS) changes over the 12-week study were analyzed with a 2×2 factorial, repeated measures ANOVA using the Proc Mixed procedure in SAS. The initial value, week 0, was used as a covariate with the main effects of HMB, ATP, and Time, and the interactions of HMB*time, ATP*time, and HMB*ATP*time in the model. The overreaching cycle of the study was also assessed by using the 2×2 factorial, repeated measures ANOVA with the Proc Mixed procedure in SAS; however, the value measured at the week 8 time point was used as a covariate with the main effects of HMB, ATP, and Time, and the interactions of HMB*time, ATP*time and HMB*ATP*time. The Least Squares Means procedure was then used to compare treatment means at each time point (post-hoc t-test). Statistical significance was determined at p≤0.05 and trends were determined between p>0.05 and p≤0.10.

Results

Participant Characteristics

There were no differences in age (Placebo=23.0±1.2, ATP=23.7±0.9 yrs., HMB=22.3±0.6, HMB-ATP=22.4±0.5), height (Placebo=180.6±2.3, ATP=179.0±1.0 cm, HMB=179.3±2.1, HMB-ATP=180.0±1.4), or body mass (Placebo=87.4±4.3, ATP=85.7±1.7, HMB=83.1±1.6, HMB-ATP=84.6±2.2) among the treatments at the start of the study.

Muscle Strength and Power

Figure 2:
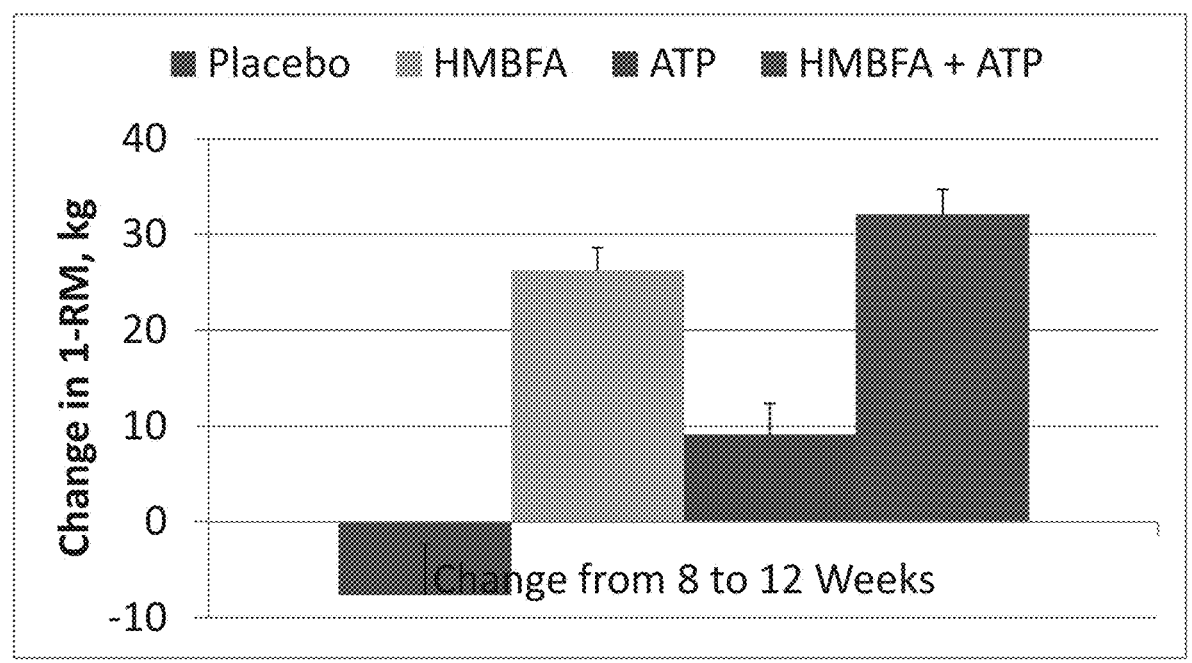
FIG. 2 shows total strength, 1-RM Change from 8 10 12 weeks.
Figure 3A:
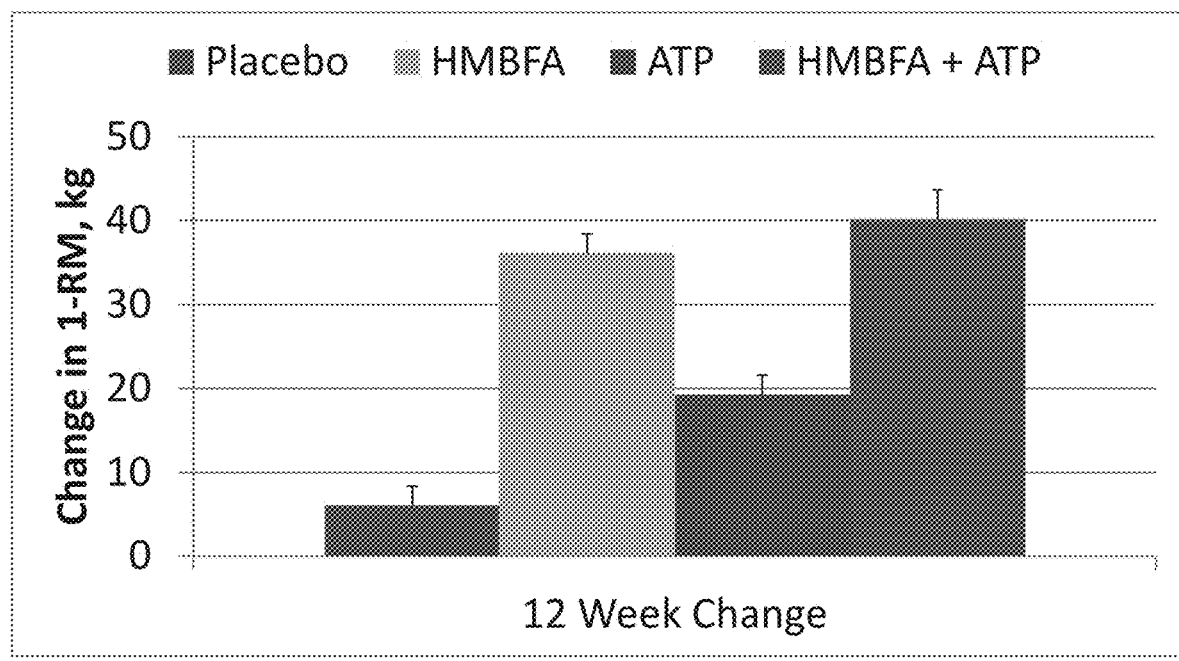
Figure 3B:
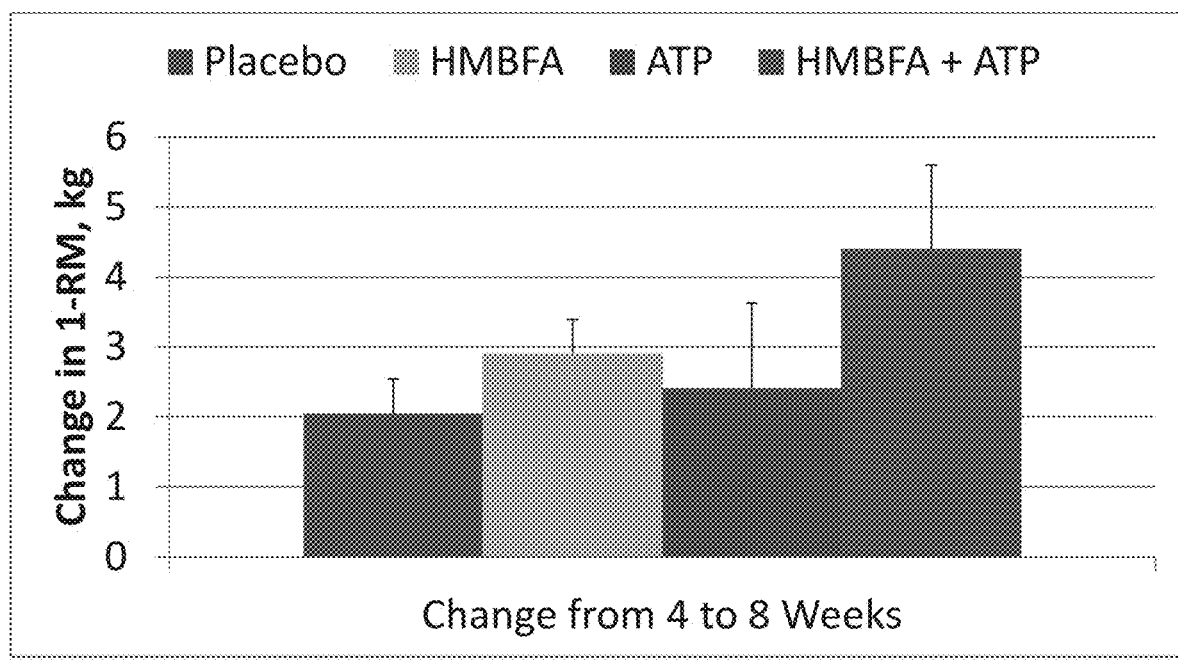

At weeks 0, 4, 8, 9, 10, and 12 during the study muscle strength (1-RM of squat, bench press, and deadlift) and muscle power (vertical jump and Wingate Peak Power, PP) were measured; both muscle strength and power increased over the 12-week study (Time, p<0.001). Supplementation with HMB, ATP and the HMB-ATP combination increased total strength gains by 77.1±5.6, 55.3±6.0, and 96.0±8.2 kg, respectively, compared with the placebo-supplemented participants who gained 22.4±7.1 kg in total strength over the 12-week study (t-test, p<0.05). FIGS. 2 and 3a-c show the synergistic effect of HMB and ATP on strength. FIG. 2 shows total strength changes from weeks 8-12. FIGS. 3a-c show individual indicators of the synergistic combination, including squat strength and bench press strength from weeks 4-8 and 4-12.

During the overreaching cycle in weeks 9 and 10, total strength declined in the placebo-supplemented participants by −4.5±0.9% from weeks 8 to 10. Total strength decreased to a lesser extent in the ATP-supplemented subjects by −2.2±0.5% from week 8 to week 10 and at week 10 the ATP-supplemented participants had increased total strength compared with the placebo-supplemented participants (t-test, p<0.05). During the overreaching cycle, HMB-supplementation attenuated the decrease in total strength (−0.5±1.2%, t-test, p<0.05 vs. placebo) and the HMB-ATP supplemented subjects unexpectedly continued to increase in strength (1.2±0.7%, t-test, p<0.05 versus placebo).

Figure 4A:
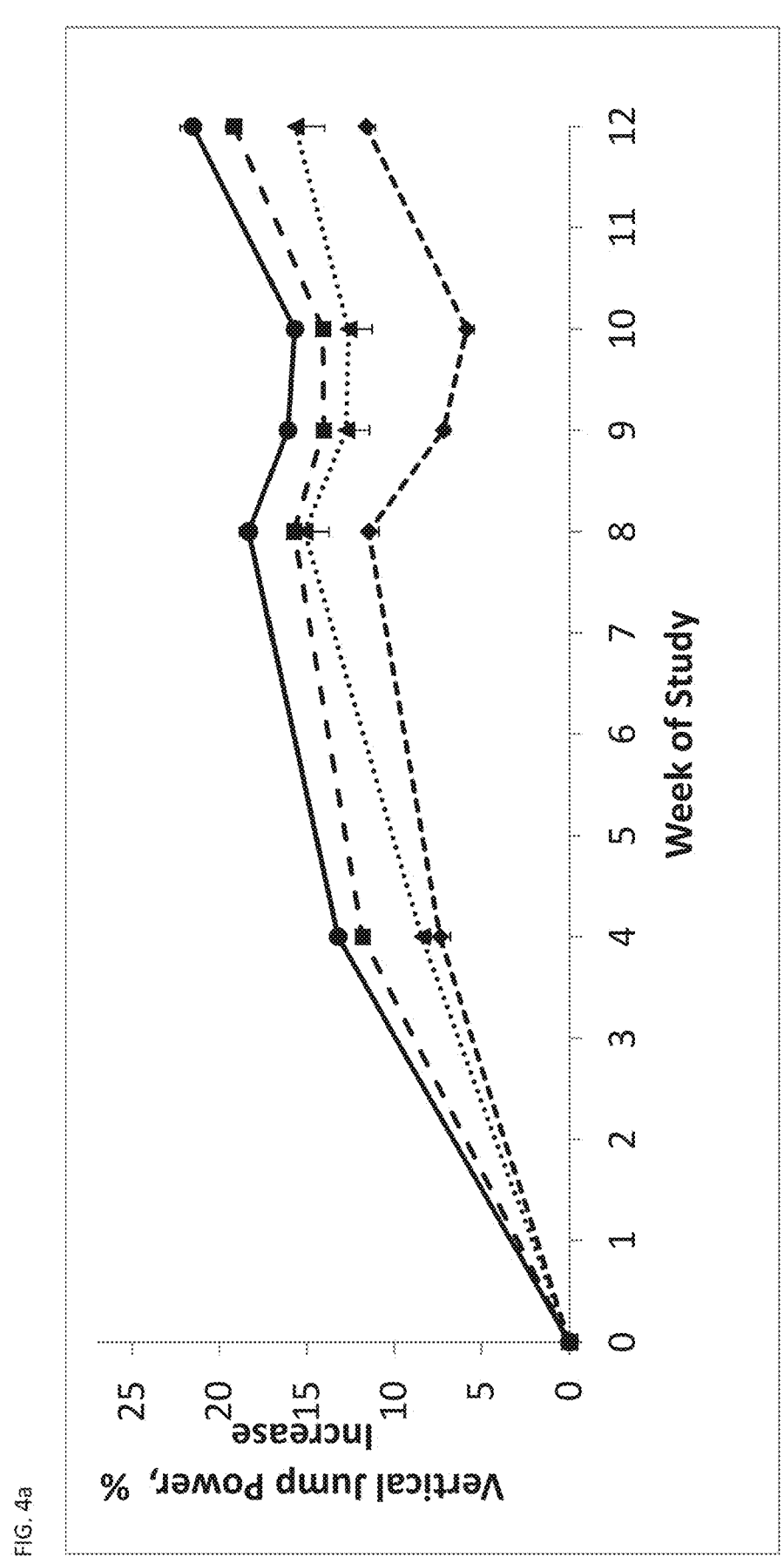
FIGS. 4a-b show the percent increase in vertical jump power and Wingate peak power.
Figure 4B:
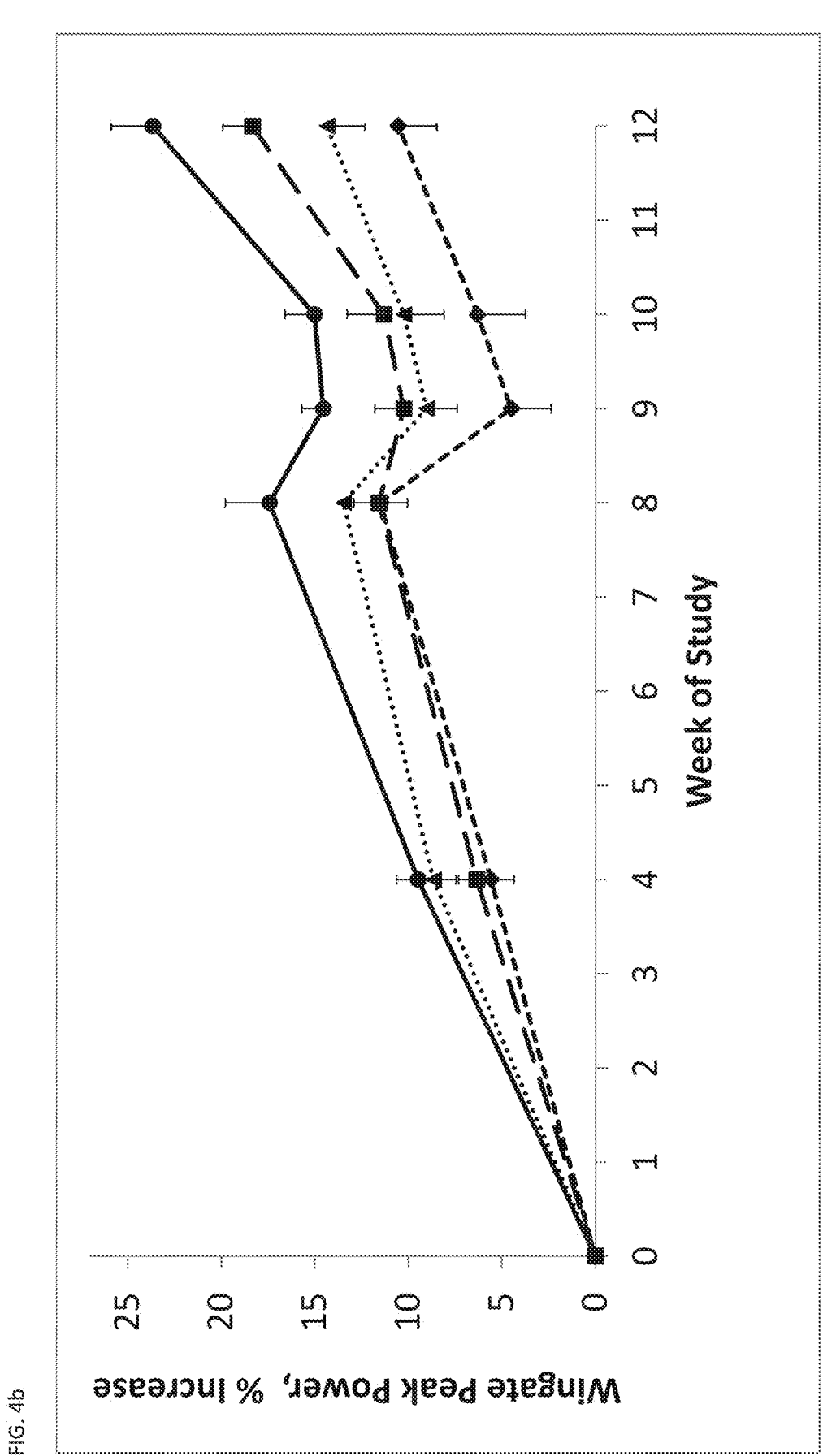

Muscular power was assessed using both the vertical jump and Wingate PP tests and results are shown in FIGS. 4a and 4b, respectively. Both of these measures of power were significantly increased during the study with HMB (HMB*time, p<0.001 for both) and with ATP supplementation (ATP*time, p<0.001 and p<0.04 for vertical jump power and Wingate PP, respectively, FIGS. 4A and 4B). Over the 12-weeks of training vertical jump power increased 614±52, 991±51, 796±75, and 1076±40 watts in placebo, HMB, ATP, and HMB-ATP supplemented groups, respectively (t-test p<0.05). The percentage increases in vertical jump power were synergistic with HMB and ATP supplemented in combination (HMB*ATP*time, p<0.004, FIG. 4a). Vertical jump power during the overreaching cycle decreased more in the placebo group, 5.0±0.4%, compared with the smaller decreases in vertical jump power for the HMB, ATP, and HMB-ATP supplemented groups, 1.4±0.4, 2.2±0.4, and 2.2±0.5%, respectively, over weeks 9 and 10 (t-test, p<0.05, FIG. 4A). During the 2-week overreaching cycle, Wingate PP decreased by 4.7±1.5, 0.3±0.9, 2.9±0.7, and 2.0±0.9% in the placebo, HMB, ATP, and HMB-ATP supplemented groups, respectively (FIG. 4B). After the first week of the increased training, HMB, ATP, and HMB-ATP supplementation resulted in the participants maintaining greater Wingate PP power than the placebo supplemented group with gains in power of 10.2±1.6, 9.0±1.6, and 14.5±1.2% from baseline, respectively (t-test, p<0.05). However, after the second week of the overreaching cycle only the HMB-ATP supplemented group had maintained significantly greater Wingate PP than the placebo-supplemented group, 1022±21 and 940±66 watts, respectively (t-test, p<0.05, FIG. 4B).

Body Composition and Muscle Hypertrophy

Resistance training resulted in increased lean body mass (LBM) and quadriceps thickness (Time, p<0.001) whereas, fat percentage was decreased with the training, (Time, p<0.001) at weeks 0, 4, 8, and 12. Supplementation with HMB increased body weight, LBM, and quadriceps thickness and decreased body fat (HMB*time, p<0.03, p<0.001, p<0.001, and p<0.001, respectively) whereas ATP supplementation increased LBM and quadriceps thickness (ATP*time, p<0.01 and 0.04, respectively). Lean body mass was increased in an additive manner by 2.1±0.5, 7.4±0.4, 4.0±0.4, and 8.5±0.8 kg in placebo, HMB, ATP, and HMB-ATP supplemented participants, respectively (t-test, p<0.05, Table 5), and fat percentage decreased by 7.0±0.6 and 8.5±0.9% in HMB and HMB-ATP supplemented participants, respectively (t-test p<0.05). Only the HMB supplementation was shown to have a significant effect on fat percentage (HMB*time p<0.001). There was no main effect of ATP*time during the study on body weight; however, the ATP alone supplemented group did have a greater body weight by week 12 of the study than the placebo-supplemented group (t-test, p<0.05). The 12-week increases in quadriceps thicknesses were 2.5±0.6, 7.1±1.2, 4.9±1.0, and 7.8±0.4 mm in placebo, HMB, ATP, and HMB-ATP supplemented participants, respectively, and HMB, ATP, and HMB-ATP supplementation resulted in a greater 12 week quadriceps thickness compared with placebo supplementation (t-test, p<0.05, Table 5).

TABLE 5

Effect of Beta-hydroxy-Beta-methylbutyrate free acid (HMB-FA) and adenosine-5'-triphosphate (ATP) supplementation on weight, lean body mass (LBM), percent body fat, and quadriceps muscle thickness in subjects performing a 12 week weight training regimen.[a]

| | Week of Study | | | | Main Effects[b] | | |
|---|---|---|---|---|---|---|---|
| | 0 | 4 | 8 | 12 | HMB-FA*Time | ATP*Time | HMB-FA*ATP*Time |
| Weight, kg | | | | | | | |
| Placebo | 87.4 ± 4.3 | 88.3 ± 4.6 | 88.7 ± 4.8 | 87.7 ± 4.7 | 0.03 | 0.63 | 0.42 |
| HMB-FA | 83.1 ± 2.8 | 83.9 ± 2.8 | 84.8 ± 2.9 | 85.0 ± 3.0[#] | | | |
| ATP | 85.7 ± 1.7 | 86.9 ± 2.0 | 87.0 ± 2.0 | 87.0 ± 2.1[#] | | | |
| HMB Plus ATP | 81.9 ± 2.1 | 82.9 ± 1.9 | 83.4 ± 1.9 | 83.6 ± 1.9[#] | | | |
| DXA LBM, kg | | | | | | | |
| Placebo | 68.5 ± 2.6 | 70.0 ± 2.3 | 71.2 ± 2.4 | 70.5 ± 2.4 | 0.001 | 0.01 | 0.80 |
| HMB-FA | 66.2 ± 2.6 | 69.2 ± 2.7[#] | 71.3 ± 2.7[#] | 73.5 ± 2.7[#] | | | |
| ATP | 67.7 ± 2.0 | 70.1 ± 1.9 | 71.4 ± 2.0 | 71.7 ± 1.9[#] | | | |
| HMB Plus ATP | 67.0 ± 1.2 | 70.5 ± 1.3[#] | 72.5 ± 1.6[#] | 75.4 ± 1.5[#] | | | |
| DXA Fat, % | | | | | | | |
| Placebo | 21.0 ± 1.1 | 19.8 ± 1.6 | 18.6 ± 1.9 | 18.6 ± 1.7 | 0.001 | 0.28 | 0.99 |
| HMB-FA | 20.4 ± 1.4 | 17.6 ± 1.4 | 15.9 ± 1.5[#] | 13.5 ± 1.5[#] | | | |
| ATP | 19.5 ± 1.8 | 18.1 ± 1.8 | 16.6 ± 1.6 | 16.0 ± 1.5 | | | |
| HMB Plus ATP | 18.0 ± 1.9 | 14.7 ± 2.2[#] | 12.7 ± 2.5[#] | 9.5 ± 2.2[#] | | | |
| Quad, mm | | | | | | | |
| Placebo | 50.2 ± 2.1 | 52.2 ± 2.3 | 52.6 ± 2.4 | 52.7 ± 2.4 | 0.001 | 0.04 | 0.45 |
| HMB-FA | 50.7 ± 1.5 | 53.6 ± 1.4 | 56.0 ± 1.4[#] | 57.8 ± 1.6[#] | | | |
| ATP | 50.9 ± 0.9 | 53.4 ± 1.3 | 54.8 ± 1.7 | 55.8 ± 1.8[#] | | | |
| HMB Plus ATP | 50.5 ± 1.2 | 53.9 ± 1.2 | 57.0 ± 1.2[#] | 58.3 ± 1.1[#] | | | |

Muscle Damage, Hormonal Status and Performance Recovery Scale

Muscle damage was assessed by blood CK, which was increased by training, particularly after the changes in training volume at the initiation of the study and at weeks 9 and 10 during the overreaching cycle (Table 6; Time, p<0.001). The initial training resulted in a 342±64% increase and the two-week overreaching cycle resulted in a 159±55% increase in CK levels in the placebo-supplemented group. Supplementation with HMB significantly attenuated the increase in CK at both the initiation of training (weeks 0 to 1) and during the overreaching cycle (weeks 9 and 10) (HMB*time, p<0.001). Supplementation with ATP alone did not attenuate the increases in CK compared with the placebo supplementation; however, HMB-ATP supplementation resulted in a significant attenuation in CK increase compared with placebo at weeks 1, 4, 9, and 10 that was similar to the effect of HMB supplementation alone (t-test, p<0.05).

The rate of muscle protein degradation was evaluated by measuring urinary 3-MH:Cr ratio (Table 6).

TABLE 6

Effect of Beta-hydroxy-Beta-methylbutyrate free acid (HMB-FA) and adenosine-5'-triphosphate (ATP) supplementation blood creatine kinase (CK), C-reactive protein (CRP), cortisol, free and total testosterone, lactate dehydrogenase (LDH) and perceived recovery score (PRS) in subjects performing a 12 week weight training regimen[a]

| | Week of Study | | | | |
|---|---|---|---|---|---|
| | 0 | 1 | 4 | 8 | 9 |
| CK, IU/L | | | | | |
| Placebo | 141 ± 12 | 582 ± 77 | 373 ± 13 | 246 ± 29 | 484 ± 52 |
| HMB-FA | 158 ± 16 | 322 ± 35[#] | 280 ± 22[#] | 255 ± 28 | 288 ± 18[#] |
| ATP | 145 ± 8 | 500 ± 71 | 324 ± 14 | 234 ± 32 | 426 ± 44 |
| HMB/ATP | 162 ± 31 | 310 ± 42[#] | 232 ± 30[#] | 212 ± 22 | 262 ± 23[#] |
| 24 h 3MH:Cr, μmol:mg | | | | | |
| Placebo | 0.127 ± 0.007 | 0.130 ± 0.003 | | 0.123 ± 0.004 | 0.134 ± 0.005 |
| HMB-FA | 0.127 ± 0.004 | 0.122 ± 0.002 | | 0.124 ± 0.008 | 0.120 ± 0.003 |
| ATP | 0.136 ± 0.008 | 0.127 ± 0.007 | | 0.143 ± 0.007[#] | 0.143 ± 0.008 |
| HMB/ATP | 0.121 ± 0.007 | 0.153 ± 0.009[#] | | 0.131 ± 0.008 | 0.131 ± 0.009 |
| CRP, mg/L | | | | | |
| Placebo | 1.9 ± 0.7 | 1.1 ± 0.1 | 1.3 ± 0.3 | 2.0 ± 0.7 | 1.6 ± 0.7 |
| HMB-FA | 1.0 ± 0.1 | 1.3 ± 0.3 | 1.0 ± 0.1 | 0.9 ± 0.01 | 1.0 ± 0.1 |
| ATP | 1.4 ± 0.4 | 1.1 ± 0.1 | 1.2 ± 0.2 | 1.9 ± 0.6 | 1.7 ± 0.6 |
| HMB/ATP | 1.2 ± 0.2 | 1.6 ± 0.6 | 1.1 ± 0.2 | 1.1 ± 0.2 | 0.9 ± 0.06 |

TABLE 6-continued

Effect of Beta-hydroxy-Beta-methylbutyrate free acid (HMB-FA) and adenosine-5'-triphosphate (ATP) supplementation blood creatine kinase (CK), C-reactive protein (CRP), cortisol, free and total testosterone, lactate dehydrogenase (LDH) and perceived recovery score (PRS) in subjects performing a 12 week weight training regimen[a]

| Cortisol, μg/dL | | | | | |
|---|---|---|---|---|---|
| Placebo | 19.7 ± 1.1 | 20.8 ± 1.3 | 19.0 ± 1.2 | 19.2 ± 0.4 | 22.0 ± 0.4 |
| HMB-FA | 21.5 ± 1.4 | 20.3 ± 1.2 | 20.9 ± 1.0 | 18.8 ± 1.5 | 19.6 ± 1.1[#] |
| ATP | 20.9 ± 1.2 | 20.5 ± 1.3 | 18.4 ± 1.4 | 19.0 ± 0.4 | 21.5 ± 0.4 |
| HMB/ATP | 20.4 ± 1.2 | 18.2 ± 2.2[#] | 17.7 ± 1.6 | 17.2 ± 1.5 | 19.1 ± 1.0[#] |
| Free Testosterone, ng/dL | | | | | |
| Placebo | 103 ± 13 | 112 ± 10 | 119 ± 6 | 111 ± 9 | 98 ± 6 |
| HMB-FA | 109 ± 10 | 104 ± 8 | 116 ± 11 | 115 ± 9 | 118 ± 8 |
| ATP | 112 ± 13 | 114 ± 9 | 118 ± 6 | 117 ± 11 | 108 ± 7 |
| HMB/ATP | 90 ± 5 | 98 ± 5 | 116 ± 10 | 103 ± 14 | 102 ± 11 |
| Total Testosterone, ng/dL | | | | | |
| Placebo | 591 ± 73 | 620 ± 58 | 625 ± 55 | 585 ± 58 | 551 ± 46 |
| HMB-FA | 708 ± 35 | 708 ± 48 | 730 ± 63 | 652 ± 35 | 752 ± 61[#] |
| ATP | 660 ± 67 | 645 ± 54 | 695 ± 60 | 645 ± 60 | 621 ± 49 |
| HMB/ATP | 568 ± 39 | 583 ± 34 | 636 ± 49 | 533 ± 51 | 581 ± 71 |
| PRS[c] | | | | | |
| Placebo | 9.1 ± 0.3 | 4.7 ± 0.4 | 7.0 ± 0.3 | 7.6 ± 0.2 | 4.8 ± 0.3 |
| HMB-FA | 9.1 ± 0.3 | 6.3 ± 0.3[#] | 7.6 ± 0.3 | 8.5 ± 0.3[#] | 8.0 ± 0.2[#] |
| ATP | 9.6 ± 0.2 | 4.9 ± 0.4 | 7.5 ± 0.3 | 8.2 ± 0.3 | 5.5 ± 0.4 |
| HMB/ATP | 9.6 ± 0.2 | 6.6 ± 0.3[#] | 8.4 ± 0.2[#] | 8.5 ± 0.3 | 7.6 ± 0.2[#] |

| | Week of Study | | Main Effects[b] | | |
|---|---|---|---|---|---|
| | 10 | 12 | HMB-FA * Time | ATP * Time | HMB-FA * ATP * Time |
| CK, IU/L | | | | | |
| Placebo | 528 ± 72 | 187 ± 21 | 0.001 | 0.89 | 0.85 |
| HMB-FA | 250 ± 14[#] | 147 ± 15 | | | |
| ATP | 449 ± 62 | 160 ± 20 | | | |
| HMB/ATP | 269 ± 31[#] | 169 ± 15 | | | |
| 24 h 3MH:Cr, μmol:mg | | | | | |
| Placebo | 0.152 ± 0.005 | | 0.05 | 0.009 | 0.005 |
| HMB-FA | 0.141 ± 0.004 | | | | |
| ATP | 0.131 ± 0.012[#] | | | | |
| HMB/ATP | 0.142 ± 0.005 | | | | |
| CRP, mg/L | | | | | |
| Placebo | 1.2 ± 0.2 | 1.6 ± 0.4 | 0.08 | 0.95 | 0.92 |
| HMB-FA | 1.8 ± 0.8[#] | 1.1 ± 0.1 | | | |
| ATP | 1.1 ± 0.1 | 1.2 ± 0.2 | | | |
| HMB/ATP | 1.1 ± 0.1 | 1.0 ± 0.1 | | | |
| Cortisol, μg/dL | | | | | |
| Placebo | 23.6 ± 0.3 | 20.3 ± 0.6 | 0.001 | 0.78 | 0.77 |
| HMB-FA | 18.6 ± 1.2[#] | 17.4 ± 1.2[#] | | | |
| ATP | 22.6 ± 0.2 | 19.7 ± 0.6 | | | |
| HMB/ATP | 17.8 ± 1.9[#] | 16.8 ± 1.4[#] | | | |
| Free Testosterone, ng/dL | | | | | |
| Placebo | 100 ± 9 | 113 ± 12 | 0.21 | 0.96 | 0.76 |
| HMB-FA | 116 ± 8 | 127 ± 8 | | | |
| ATP | 110 ± 10 | 125 ± 13 | | | |
| HMB/ATP | 115 ± 12 | 118 ± 9 | | | |
| Total Testosterone, ng/dL | | | | | |
| Placebo | 536 ± 88 | 605 ± 72 | 0.18 | 0.93 | 0.93 |
| HMB-FA | 701 ± 34 | 728 ± 39 | | | |
| ATP | 592 ± 84 | 673 ± 69 | | | |
| HMB/ATP | 617 ± 37 | 655 ± 27 | | | |

TABLE 6-continued

Effect of Beta-hydroxy-Beta-methylbutyrate free acid (HMB-FA) and adenosine-5'-triphosphate (ATP) supplementation blood creatine kinase (CK), C-reactive protein (CRP), cortisol, free and total testosterone, lactate dehydrogenase (LDH) and perceived recovery score (PRS) in subjects performing a 12 week weight training regimen[a]

| PRS[c] | | | | | |
|---|---|---|---|---|---|
| Placebo | 4.4 ± 0.3 | 7.6 ± 0.2 | 0.001 | 0.79 | 0.06 |
| HMB-FA | 7.7 ± 0.2[#] | 9.5 ± 0.2[#] | | | |
| ATP | 5.5 ± 0.4[#] | 8.6 ± 0.4[#] | | | |
| HMB/ATP | 7.4 ± 0.2[#] | 9.6 ± 0.2[#] | | | |

[a]Mean ± SEM for n = 10 placebo, n = 11 HMB (3 g HMB free acid/d in three 1 g doses daily), n = 11 ATP (one 400 mg dose of ATP in the morning), and n = 8 for HMB plus ATP (3 g HMB free acid/d in three 1 g doses daily and one 400 mg dose of ATP in the morning) supplemented subjects.
[b]Probability of treatment by time difference between the treatments over the 12-week study. The mixed model 2 x 2 Factorial Repeat ANOVA (SAS ®) was used, with the value for week 0 used as a covariate.
[c]Perceived recovery score is rated on the participants feeling of recovery from the last workout on a scale of 0-10.
[#]Significantly different than corresponding placebo, t-test (p < 0.05).

C-Reactive protein levels were not significantly affected by any of the treatments during the study. A trend was observed for an HMB effect (HMB*time, p<0.08) and HMB supplementation resulted in a greater mean CRP value at week 10 than did placebo supplementation (t-test, p<0.05). Supplementation with ATP did not affect cortisol levels, while HMB supplementation decreased cortisol levels during the study (HMB*time, p<0.001, Table 6). Supplementation with HMB alone resulted in decreased cortisol levels at weeks 9, 10, and 12 during the overreaching and taper cycles (t-test, p<0.05) and supplementation with HMB-ATP resulted in decreased cortisol levels after both the initiation of training, week 1, and the overreaching and taper cycles, weeks 9, 10, and 12 (t-test p<0.05). There were no main effect differences of either HMB or ATP on either free or total testosterone.

Muscle recovery and readiness to train in the next training session were measured by perceived recovery score (PRS, Table 6). Supplementation with HMB and HMB-ATP resulted in improved PRS over the 12-week study (HMB*time, p<0.001). While no main effect of ATP supplementation was observed, ATP-supplemented participants had improved PRS scores after the overreaching cycle at weeks 10 and 12 compared with placebo-supplemented participants (t-test, p<0.05). At week 4, the HMB/ATP-supplemented group was the only group with a significantly improved PRS compared with the placebo-supplementation (t-test, p<0.05). A trend for an HMB and ATP interaction, indicating a synergistic effect of the combined supplementation on PRS, was also observed (HMB*ATP*time, p<0.06).

The experimental examples demonstrate that HMB-ATP supplementation results in increased strength and power adaptations compared to just HMB or ATP supplementation alone, and this increase is synergistic.

Further, the results indicated greater increases in LBM and muscle thickness in the HMB-ATP, HMB, and ATP groups as compared to the placebo and the administration of HMB-ATP has greater effects on muscle hypertrophy and lean body mass compared to just HMB or ATP supplementation alone.

The administration of HMB-ATP results in increases in LBM, muscle hypertrophy, strength, and power. These increases are, in the instances of strength and power, synergistic, and in the instances of lean body mass and muscle hypertrophy, additive. Moreover, when faced with greater training frequencies, as demonstrated with the overreaching cycle of training, HMB-ATP prevents typical declines in performance that are characteristic of overreaching. All of these results were unexpected and surprising.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention. The terms subject and animal are used interchangeably throughout this application and are in no way limited to one term or the other.

LITERATURE CITED

1. Nissen, S. L. & Sharp, R. L. Effect of dietary supplements on lean mass and strength gains with resistance exercise: a meta-analysis. J Appl. Physiol 94: 651-659, 2003.
2. Panton, L. B., Rathmacher, J. A., Baler, S. & Nissen, S. Nutritional supplementation of the leucine metabolite b-hydroxy b-methylbutyrate (HMB) during resistance training. Nutr. 16(9): 734-739, 2000.
3. Nissen, S., Sharp, R., Ray, M., Rathmacher, J. A., Rice, J., Fuller, J. C., Jr., Connelly, A. S. & Abumrad, N. N. Effect of the leucine metabolite b-hydroxy b-methylbutyrate on muscle metabolism during resistance-exercise training. J. Appl. Physiol. 81(5): 2095-2104, 1996.
4. Eubanks May, P., Barber, A., Hourihane, A., D'Olimpio, J. T. & Abumrad, N. N. Reversal of cancer-related wasting using oral supplementation with a combination of b-hydroxy-b-methylbutyrate, arginine, and glutamine. Am. J. Surg. 183: 471-479, 2002.
5. Clark, R. H., Feleke, G., Din, M., Yasmin, T., Singh, G., Khan, F. & Rathmacher, J. A. Nutritional treatment for acquired immunodeficiency virus-associated wasting using b-hydroxy-b-methylbutyrate, glutamine and arginine: A randomized, double-blind, placebo-controlled study. JPEN J Parenter Enteral Nutr 24(3): 133-139, 2000.
6. Gallagher, P. M., Carrithers, J. A., Godard, M. P., Schulze, K. E. & Trappe, S. W. b-Hydroxy-b-methylbutyrate ingestion, Part I: Effects on strength and fat free mass. Med Sci Sports Exerc 32(12): 2109-2115, 2000.
7. Jówko, E., Ostaszewski, P., Jank, M., Sacharuk, J., Zieniewicz, A., Wilczak, J. & Nissen, S. Creatine and b-hydroxy-b-methylbutyrate (HMB) additively increases lean body mass and muscle strength during a weight training program. Nutr. 17: 558-566, 2001.
8. Knitter, A. E., Panton, L., Rathmacher, J. A., Petersen, A. & Sharp, R. Effects of b-hydroxy-b-methylbutyrate on muscle damage following a prolonged run. J. Appl. Physiol. 89(4): 1340-1344, 2000.
9. Ostaszewski, P., Kostiuk, S., Balasinska, B., Jank, M., Papet, I. & Glomot, F. The leucine metabolite 3-hydroxy-3-methylbutyrate (HMB) modifies protein turnover in muscles of the laboratory rats and domestic chicken in vitro. J. Anim. Physiol. Anim. Nutr. (Swiss) 84: 1-8, 2000.
10. Russell, S. T. & Tisdale, M. J. Mechanism of attenuation by beta-hydroxy-beta-methylbutyrate of muscle protein degradation induced by lipopolysaccharide. Mol. Cell Biochem. 330(1-2): 171-179, 2009.
11. Eley, H. L., Russell, S. T. & Tisdale, M. J. Attenuation of depression of muscle protein synthesis induced by lipopolysaccharide, tumor necrosis factor and angiotensin II by b-hydroxy-b-methylbutyrate. Am. J. Physiol Endocrinol. Metab 295: E1409-E1416, 2008.
12. Eley, H. L., Russell, S. T., Baxter, J. H., Mukerji, P. & Tisdale, M. J. Signaling pathways initiated by b-hydroxy-b-methylbutyrate to attenuate the depression of protein synthesis in skeletal muscle in response to cachectic stimuli. Am. J. Physiol Endocrinol. Metab 293: E923-E931, 2007.
13. Smith, H. J., Wyke, S. M. & Tisdale, M. J. Mechanism of the attenuation of proteolysis-inducing factor stimulated protein degradation in muscle by beta-hydroxy-beta-methylbutyrate. Cancer Res. 64: 8731-8735, 2004.
14. Smith, H. J., Mukerji, P. & Tisdale, M. J. Attenuation of proteasome-induced proteolysis in skeletal muscle by b-hydroxy-b-methylbutyrate in cancer-induced muscle loss. Cancer Res. 65: 277-283, 2005.
15. Eley, H. L., Russell, S. T. & Tisdale, M. J. Mechanism of Attenuation of Muscle Protein Degradation Induced by Tumor Necrosis Factor Alpha and Angiotensin II by beta-Hydroxy-beta-methylbutyrate. Am. J. Physiol Endocrinol. Metab 295: E1417-E1426, 2008.
16. Fuller, J. C., Jr., Baier, S., Flakoll, P. J., Nissen, S. L., Abumrad, N. N. & Rathmacher, J. A. Vitamin D status affects strength gains in older adults supplemented with a combination of b-hydroxy-b-methylbutyrate, arginine and lysine: A cohort study. JPEN 35: 757-762, 2011.
17. Sousa, M. F., Abumrad, N. N., Martins, C., Nissen, S. & Riella, M. C. Calcium b-hydroxy-b-methylbutyrate. Potential role as a phosphate binder in uremia: In vitro study. Nephron 72: 391-394, 1996.
18. Fuller, J. C., Jr., Sharp, R. L., Angus, H. F., Baier, S. M. & Rathmacher, J. A. Free acid gel form of beta-hydroxy-beta-methylbutyrate (HMB) improves HMB clearance from plasma in human subjects compared with the calcium HMB salt. Br. J Nutr. 105: 367-372, 2011.
19. Kushmerick, M. J. & Conley, K. E. Energetics of muscle contraction: the whole is less than the sum of its parts. Biochem. Soc. Trans. 30: 227-231, 2002.
20. Burnstock, G., Knight, G. E. & Greig, A. V. Purinergic signaling in healthy and diseased skin. J Invest Dermatol. 132: 526-546, 2012.
21. Agteresch, H. J., Dagnelie, P. C., van den Berg, J. W. & Wilson, J. H. Adenosine triphosphate: established and potential clinical applications. Drugs 58: 211-232, 1999.
22. Sawynok, J. & Sweeney, M. I. The role of purines in nociception. Neuroscience 32: 557-569, 1989.
23. Yajima, H., Sato, J., Giron, R., Nakamura, R. & Mizumura, K. Inhibitory, facilitatory, and excitatory effects of ATP and purinergic receptor agonists on the activity of rat cutaneous nociceptors in vitro. Neurosci. Res. 51: 405-416, 2005.
24. Khakh, B. S. & Henderson, G. ATP receptor-mediated enhancement of fast excitatory neurotransmitter release in the brain. Mol. Pharmacol. 54: 372-378, 1998.
25. Ellis, C. G., Milkovich, S. & Goldman, D. What is the Efficiency of ATP Signaling from Erythrocytes to Regulate Distribution of 0(2) Supply within the Microvasculature? Microcirculation, 2012.
26. Gergs, U., Boknik, P., Schmitz, W., Simm, A., Silber, R. E. & Neumann, J. A positive inotropic effect of adenosine in cardiac preparations of right atria from diseased human hearts. Naunyn Schmiedebergs Arch. Pharmacol. 379: 533-540, 2009.
27. Gergs, U., Boknik, P., Schmitz, W., Simm, A., Silber, R. E. & Neumann, J. A positive inotropic effect of ATP in the human cardiac atrium. Am. J Physiol Heart Circ. Physiol 294: H1716-H1723, 2008.
28. Kichenin, K., Decollogne, S., Angignard, J. & Seman, M. Cardiovascular and pulmonary response to oral administration of ATP in rabbits. J Appl. Physiol 88: 1962-1968, 2000.
29. Heinonen, I., Kemppainen, J., Kaskinoro, K., Peltonen, J. E., Sipila, H. T., Nuutila, P., Knuuti, J., Boushel, R. & Kalliokoski, K. K. Effects of adenosine, exercise, and moderate acute hypoxia on energy substrate utilization of human skeletal muscle. Am. J. Physiol Regul. Integr. Comp Physiol 302: R385-R390, 2012.
30. Yegutkin, G. G. Nucleotide- and nucleoside-converting ectoenzymes: Important modulators of purinergic signaling cascade. Biochim. Biophys. Acta 1783: 673-694, 2008.
31. Nyberg, M., Mortensen, S. P., Thaning, P., Saltin, B. & Hellsten, Y. Interstitial and plasma adenosine stimulate nitric oxide and prostacyclin formation in human skeletal muscle. Hypertension 56: 1102-1108, 2010.
32. Jordan, A. N., Jurca, R., Abraham, E. H., Salikhova, A., Mann, J. K., Morss, G. M., Church, T. S., Lucia, A. & Earnest, C. P. Effects of oral ATP supplementation on anaerobic power and muscular strength. Med. Sci. Sports Exerc. 36: 983-990, 2004.
33. Arts, I. C., Coolen, E. J., Bours, M. J., Huyghebaert, N., Cohen Stuart, M. A., Bast, A. & Dagnelie, P. C. Adenosine 5'-triphosphate (ATP) supplements are not orally bioavailable: a randomized, placebocontrolled cross-over trial in healthy humans. J. Int. Soc. Sports Nutr. 9: 16, 2012.
34. Coolen, E. J., Arts, I. C., Bekers, 0., Vervaet, C., Bast, A. & Dagnelie, P. C. Oral bioavailability of ATP after prolonged administration. Br. J. Nutr. 105: 357-366, 2011.
35. Synnestvedt, K., Furuta, G. T., Comerford, K. M., Louis, N., Karhausen, J., Eltzschig, H. K., Hansen, K. R., Thompson, L. F. & Colgan, S. P. Ecto-5'-nucleotidase (CD73) regulation by hypoxia-inducible factor-1 mediates permeability changes in intestinal epithelia. J Clin. Invest 110: 993-1002, 2002.
36. Kraemer, W. J., Hatfield, D. L., Volek, J. S., Fragala, M. S., Vingren, J. L., Anderson, J. M., Spiering, B. A., Thomas, G. A., Ho, J. Y. et al. Effects of Amino Acids Supplement on Physiological Adaptations to Resistance Training. Med. Sci. Sports Exerc. 41: 1111-1121, 2009.
37. Monteiro, A. G., Aoki, M. S., Evangelista, A. L., Alveno, D. A., Monteiro, G. A., Picarro, I. C. & Ugrinowitsch, C. Nonlinear periodization maximizes strength gains in split resistance training routines. J Strength. Cond. Res. 23: 1321-1326, 2009.

38. Laurent, C. M., Green, J. M., Bishop, P. A., Sjokvist, J., Schumacker, R. E., Richardson, M. T. & Curtner-Smith, M. A practical approach to monitoring recovery: development of a perceived recovery status scale. *J Strength. Cond. Res.* 25: 620-628, 2011.

39. Rathmacher, J. A., Link, G. A., Flakoll, P. J. & Nissen, S. L. Gas chromatographic-mass spectrometric analysis of stable isotopes of 3-methylhistidine in biological fluids: application to plasma kinetics in vivo. *Biol. Mass Spectrom.* 21: 560-566, 1992.

40. Barnes J N, Trombold J R, Dhindsa M, Lin H F, and Tanaka H. Arterial stiffening following eccentric exercise-induced muscle damage. *Journal of applied physiology* 109: 1102-1108, 2010.

41. Cormie P, McGuigan M R, and Newton R U. Developing maximal neuromuscular power: Part 1--biological basis of maximal power production. *Sports medicine* 41: 17-38, 2011.

42. Cormie P, McGuigan M R, and Newton R U. Developing maximal neuromuscular power: part 2—training considerations for improving maximal power production. *Sports medicine* 41: 125-146, 2011.

43. Dufour S P, Patel R P, Brandon A, Teng X, Pearson J, Barker H, Ali L, Yuen A H, Smolenski R T, and Gonzalez-Alonso J. Erythrocyte-dependent regulation of human skeletal muscle blood flow: role of varied oxyhemoglobin and exercise on nitrite, S-nitrosohemoglobin, and ATP. *American journal of physiology Heart and circulatory physiology* 299: H1936-1946, 2010.

44. Gilbert G and Lees A. Changes in the force development characteristics of muscle following repeated maximum force and power exercise. *Ergonomics* 48: 1576-1584, 2005.

45. Gonzalez-Alonso J. ATP as a mediator of erythrocyte-dependent regulation of skeletal muscle blood flow and oxygen delivery in humans. *The Journal of physiology* 590: 5001-5013, 2012.

46. Gonzalez-Alonso J, Mortensen S P, Dawson E A, Secher N H, and Damsgaard R. Erythrocytes and the regulation of human skeletal muscle blood flow and oxygen delivery: role of erythrocyte count and oxygenation state of haemoglobin. *The Journal of physiology* 572: 295-305, 2006.

47. Gonzalez-Alonso J, Mortensen S P, Jeppesen T D, Ali L, Barker H, Damsgaard R, Secher N H, Dawson E A, and Dufour S P. Haemodynamic responses to exercise, ATP infusion and thigh compression in humans: insight into the role of muscle mechanisms on cardiovascular function. *The Journal of physiology* 586: 2405-2417, 2008.

48. Halson S L and Jeukendrup A E. Does overtraining exist? An analysis of overreaching and overtraining research. *Sports medicine* 34: 967-981, 2004.

49. Hunga W, Liub T-H, Chenc C-Y, and Chang C-K. Effect of [beta]-hydroxy-[beta]-methylbutyrate Supplementation During Energy Restriction in Female Judo Athletes. *Journal of Exercise Science and Fitness* 8: 50-53, 2010.

50. Jowko E, Ostaszewski P, Jank M, Sacharuk J, Zieniewicz A, Wilczak J, and Nissen S. Creatine and beta-hydroxy-beta-methylbutyrate (HMB) additively increase lean body mass and muscle strength during a weight-training program. *Nutrition* 17: 558-566, 2001.

51. Kraemer W J and Ratamess N A. Fundamentals of resistance training: progression and exercise prescription. *Med Sci Sports Exerc* 36: 674-688, 2004.

52. Rathmacher J A, Fuller J C, Jr., Baier S M, Abumrad N N, Angus H F, and Sharp R L. Adenosine-5'-triphosphate (ATP) supplementation improves low peak muscle torque and torque fatigue during repeated high intensity exercise sets. *Journal of the International Society of Sports Nutrition* 9: 48, 2012.

53. Robbins D W and Docherty D. Effect of loading on enhancement of power performance over three consecutive trials. *Journal of strength and conditioning research/National Strength & Conditioning Association* 19: 898-902, 2005.

54. Sprague R S, Bowles E A, Achilleus D, Stephenson A H, Ellis C G, and Ellsworth M L. A selective phosphodiesterase 3 inhibitor rescues low P02-induced ATP release from erythrocytes of humans with type 2 diabetes: implication for vascular control. *American journal of physiology Heart and circulatory physiology* 301: H2466-2472, 2011.

55. Thomson J S, Watson P E, and Rowlands D S. Effects of nine weeks of beta-hydroxy-beta-methylbutyrate supplementation on strength and body composition in resistance trained men. *Journal of strength and conditioning research/National Strength & Conditioning Association* 23: 827-835, 2009.

56. Trautmann A. Extracellular ATP in the immune system: more than just a "danger signal". *Science signaling* 2: pe6, 2009.

57. van Someren K A, Edwards A J, and Howatson G. Supplementation with beta-hydroxy-beta-methylbutyrate (HMB) and alpha-ketoisocaproic acid (KIC) reduces signs and symptoms of exercise-induced muscle damage in man. *International journal of sport nutrition and exercise metabolism* 15: 413-424, 2005.

58. Wilkinson D J, Hossain T, Hill D S, Phillips B E, Crossland H, Williams J, Loughna P, Churchward-Venne T A, Breen L, Phillips S M, Etheridge T, Rathmacher J A, Smith K, Szewczyk N J, and Atherton P J. Effects of Leucine and its metabolite, beta-hydroxy-beta-methylbutyrate (HMB) on human skeletal muscle protein metabolism. *The Journal of physiology,* 2013.

59. Wilson G J, Wilson J M, and Manninen A H. Effects of beta-hydroxy-beta-methylbutyrate (HMB) on exercise performance and body composition across varying levels of age, sex, and training experience: A review. *Nutr Metab (Lond)* 5: 1, 2008.

60. Wilson J M, Duncan N M, Marin P J, Brown L E, Loenneke J P, Wilson S M, Jo E, Lowery R P, and Ugrinowitsch C. Meta-Analysis of Post Activation Potentiation and Power: Effects of Conditioning Activity, Volume, Gender, Rest Periods, and Training Status. *Journal of strength and conditioning research/National Strength & Conditioning Association,* 2012.

61. Wilson J M, Lowery R P, Joy J M, Walters J, Baier S, Fuller J C, Jr., Stout J, Norton L, Sikorski E M, Wilson S M-C, Duncan N, Zanchi N, and Rathmacher J. β-Hydroxy-β-Methylbutyrate Free Acid Reduces Markers of Exercise Induced Muscle Damage and Improves Recovery in Resistance Trained Men. *British Journal of Nutrition* In Press.

The invention claimed is:

1. A method for increasing the strength of a human in need thereof comprising the steps of administering to said human a synergistic combination of from about 0.5 to about 30 g of β-hydroxy-β-methylbutyric acid (HMB) and from about 10 mg to about 80 g ATP, wherein upon said administration of HMB and adenosine triphosphate (ATP) to the human, said strength is increased.

2. The method of claim 1, wherein said HMB is selected from the group consisting of its free acid form, its salt, its ester and its lactone.

3. The method of claim 1, wherein the HMB and the ATP are administered in separate delivery carriers.

4. The method of claim 1, wherein the HMB and the ATP are administered concomitantly.

5. The method of claim 1, wherein the human is an exercising human.

6. The method of claim 5, wherein the exercise is resistance training.

7. A method for increasing the power of a human in need thereof comprising the steps of administering to said human a synergistic combination of from about 0.5 to about 30 g of β-hydroxy-β-methylbutyric acid (HMB) and from about 10 mg to about 80 g ATP, wherein upon said administration of HMB and adenosine triphosphate (ATP) to the human, said power is increased.

8. The method of claim 7, wherein said HMB is selected from the group consisting of its free acid form, its salt, its ester and its lactone.

9. The method of claim 7, wherein the HMB and the ATP are administered in separate delivery carriers.

10. The method of claim 7, wherein the HMB and the ATP are administered concomitantly.

11. The method of claim 7, wherein the human is an exercising human.

12. The method of claim 11, wherein the exercise is resistance training.

13. A method for increasing the muscular endurance of a human in need thereof comprising the steps of administering to said human a synergistic combination of from about 0.5 to about 30 g of β-hydroxy-β-methylbutyric acid (HMB) and from about 10 mg to about 80 g ATP, wherein upon said administration of HMB and adenosine triphosphate (ATP) to the human, said muscular endurance is increased.

14. The method of claim 13, wherein said HMB is selected from the group consisting of its free acid form, its salt, its ester and its lactone.

15. The method of claim 13, wherein the HMB and the ATP are administered in separate delivery carriers.

16. The method of claim 13, wherein the HMB and the ATP are administered concomitantly.

17. The method of claim 13, wherein the human is an exercising human.

18. The method of claim 17, wherein the exercise is resistance training.

* * * * *